United States Patent
Ackermann et al.

(10) Patent No.: US 6,965,048 B2
(45) Date of Patent: Nov. 15, 2005

(54) HYDROXYALKYLAMIDE DERIVATIVES

(75) Inventors: Jean Ackermann, Riehen (CH);
Johannes Aebi, Basel (CH); Henrietta Dehmlow, Grenzach-Wyhlen (DE);
Olivier Morand, Hegenheim (FR);
Narendra Panday, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/883,431

(22) Filed: Jul. 1, 2004

(65) Prior Publication Data

US 2005/0009906 A1 Jan. 13, 2005

(30) Foreign Application Priority Data

Jul. 2, 2003 (EP) .............................. 03014477

(51) Int. Cl.⁷ .................. C07C 271/44; A61K 31/27
(52) U.S. Cl. .................. 560/115; 546/226; 564/80; 564/134; 564/138; 564/142; 514/488; 514/330; 514/602
(58) Field of Search .............. 560/115; 564/80, 564/134, 138, 142; 546/226; 514/488, 300, 602

(56) References Cited

U.S. PATENT DOCUMENTS

| 5,495,048 A | 2/1996 | Aebi et al. |
| 5,574,071 A | 11/1996 | Aebi et al. |
| 5,637,771 A | 6/1997 | Aebi et al. |
| 5,843,973 A | 12/1998 | Ishihara et al. |
| 6,022,969 A | 2/2000 | Rice et al. |

FOREIGN PATENT DOCUMENTS

| EP | 0370498 A2 | 5/1990 |
| EP | 636367 | 2/1995 |
| WO | WO 02/14267 A1 | 2/2002 |

OTHER PUBLICATIONS

Schmalhofer et al, Biochemistry, vol 41, pp. 7781–7794, 2002.*

Miao et al, Bioorg. Med. Chem. Lett., 13, pp. 1161–1164, 2003.*

Moreno, A. et al, European Journal of Medicinal Chemistry, Editions Scientifique Elsevier, Paris, FR, vol. 39, No. 1, pp. 49–58 XP004492418 (2004).

* cited by examiner

*Primary Examiner*—Shailendra Kumar
(74) *Attorney, Agent, or Firm*—George W. Johnston; Patricia S. Rocha-Tramaloni; David E. Wildman

(57) ABSTRACT

The present invention relates to compounds of formula (I)

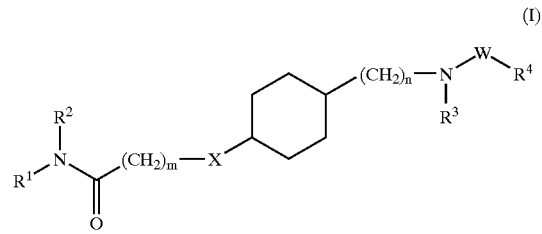

wherein $R^1$, $R^2$, $R^3$, $R^4$, X, W, m and n are as defined hereinabove. The compounds are useful for the treatment and/or prophylaxis of diseases which are associated with 2,3-oxidosqualene-lanosterol cyclase such as hypercholesterolemia, hyperlipemia, arteriosclerosis, vascular diseases, mycoses, parasite infections, gallstones, tumors and/or hyperproliferative disorders, and treatment and/or prophylaxis of impaired glucose tolerance and diabetes.

22 Claims, No Drawings

HYDROXYALKYLAMIDE DERIVATIVES

FIELD OF THE INVENTION

The present invention is related to novel hydroxyalkylamide derivatives of formula (I)

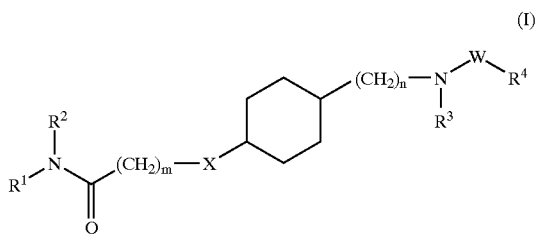

wherein $R^1$, $R^2$, $R^3$, $R^4$, W, X, m and n are as defined herein below, as well as to a process for the manufacture of a compound of formula (I), a pharmaceutical composition comprising a compound of formula (I), and a method for the treatment and/or prophylaxis of diseases which are associated with OSC, which method comprises administering to a patient in need thereof a therapeutically effective amount of at least one compound of formula (I). These compounds are useful, inter alia, in the treatment or prevention of hypercholesterolemia, hyperlipemia, arteriosclerosis, vascular diseases, mycoses, parasite infections, gallstones, tumors, hyperproliferative disorders, impaired glucose tolerance, diabetes or neurodegenerative disease.

BACKGROUND OF THE INVENTION

The compounds of the present invention inhibit 2,3-oxidosqualene-lanosterol cyclase (EC 5.4.99.) which is required for the biosynthesis of cholesterol, ergosterol and other sterols. Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established [Gotto et al., Circulation 81:1721–1733 (1990); Stein et al., Nutr. Metab. Cardiovasc. Dis. 2:113–156 (1992); Illingworth, Med. Clin. North. Am. 84:23–42 (2000)]. Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C [Ross et al., Arch. Intern. Med. 159:1793–1802 (1999)].

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fibrate proved to be very efficacious in lowering LDL-C and triglycerides [Ellen and McPherson, J. Cardiol. 81:60B-65B (1998)], but safety of such a combination remains an issue [Shepherd, Eur. Heart J. 16:5–13 (1995)]. A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses [Davignon et al., Can. J. Cardiol. 8:843–864 (1992); Pederson and Tobert, Drug Safety 14:11–24 (1996)].

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug [Morand et al., J. Lipid Res. 38:373–390 (1997); Mark et al., J. Lipid Res. 37:148–158 (1996)]. OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content. The compounds described in EP 636,367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol [Peffley et al., Biochem. Pharmacol. 56:439–449 (1998); Nelson et al., J. Biol. Chem. 256:1067–1068 (1981); Spencer et al., J. Biol. Chem. 260:13391–13394 (1985); Panini et al., J. Lipid Res. 27:1190–1204 (1986); Ness et al., Arch. Biochem. Biophys. 308:420–425 (1994)]. This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR [Janowski et al., Proc. Natl. Acad. Sci. USA 96:266–271 (1999)]. Considering that 24(S),25-epoxycholesterol is a by-product of inhibition of OSC it is hypothesized that the OSC inhibitors of the present invention could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels [Venkateswaran et al., J. Biol. Chem.

275:14700–14707 (2000); Wang et al., J. Biol. Chem. 275:33053–33058 (2000); Ordovas, Nutr Rev 58:76–79 (2000), Schmitz and Kaminsky, Front Biosci 6:D505-D514 (2001)], and/or inhibit intestinal cholesterol absorption [Mangelsdorf, XIIth International Symposium on Atherosclerosis, Stockholm, June 2000)]. In addition, possible cross talks between fatty acid and cholesterol metabolism mediated by liver LXR have been hypothesized [Tobin et al., Mol. Endocrinol. 14:741–752 (2000)].

The present compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of neurodegenerative diseases, mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutic use to improve glucose tolerance in order to treat and/or prevent related diseases such as diabetes. The compounds of the present invention further exhibit improved pharmacological properties compared to known compounds.

SUMMARY OF THE INVENTION

The present invention relates to a compound of formula (I)

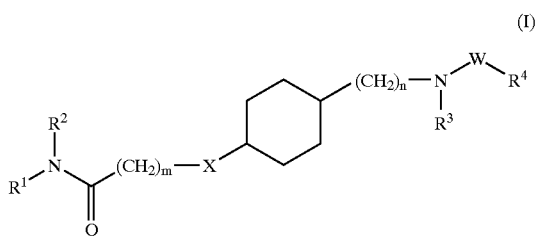

wherein
$R^1$ is hydrogen or lower-alkyl;
$R^2$ is selected from hydroxy-lower-alkyl, hydroxy-lower-alkyl substituted with lower-alkyl, hydroxy-cycloalkyl, hydroxy-cycloalkyl substituted with lower-alkyl, carbamoyl-lower-alkyl and carbamoyl-lower alkyl substituted with lower-alkyl; or
$R^1$ and $R^2$ are bonded to each other to form a ring together with the nitrogen atom to which they are attached and —$R^1$—$R^2$— is lower-alkylene which is substituted with a group selected from hydroxy, hydroxy-lower-alky and carbamoyl;
$R^3$ is hydrogen or lower-alkyl;
$R^4$ is aryl;
W is selected from CO, COO, CONR$^5$, CSO, CSNR$^5$, SO$_2$, and SO$_2$NR$^5$;
$R^5$ is hydrogen or lower-alkyl;
X is selected from a single bond, O, —CH=CH—, and —C≡C—;
m is 0, 1, 2, 3 or 4, wherein m is not 0 if X is O; and
n is 0, 1, 2 or 3, wherein m+n is not more than 5.

Another embodiment of this invention relates to a process for the manufacture of a compound of formula (I).

Yet another embodiment of this invention relates to a pharmaceutical composition comprising a compound of formula (I).

Yet another embodiment of this invention relates to a method for the treatment or prophylaxis of diseases which are associated with OSC such as hypercholesterolemia, hyperlipemia, arteriosclerosis, vascular diseases, mycoses, parasite infections, gallstones, tumors, hyperproliferative disorders, impaired glucose tolerance, diabetes, or neurodegenerative disease, which method comprises administering to a patient in need thereof a therapeutically effective amount of at least one compound of formula (I).

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl. The term "thio-alkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and 2 to 20, preferably 2 to 16 carbon atoms, more preferably 2 to 10 carbon atoms. Lower-alkenyl groups as described below also are preferred alkenyl groups. The term "lower-alkenyl" refers to a straight-chain or branched hydrocarbon residue comprising an olefinic bond and 2 to 7, preferably 2 to 4 carbon atoms, such as e.g. 2-propenyl.

The term "alkynyl", alone or in combination with other groups, stands for a straight-chain or branched hydrocarbon residue comprising a triple bond and 2 to 20, preferably 2 to 16 carbon atoms, more preferably 2 to 10 carbon atoms. Lower-alkynyl groups as described below also are preferred alkynyl groups. The term "lower-alkynyl" refers to a straight-chain or branched hydrocarbon residue comprising a triple bond and 2 to 7, preferably 2 to 4 carbon atoms, such as e.g. 2-propinyl.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms.

Straight chain alkylene or lower-alkylene groups are preferred.

The term "aryl" relates to the phenyl or naphthyl group, preferably the phenyl group, which can optionally be substituted by 1 to 3 substituents independently selected from the group consisting of lower-alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl. Preferred substituents are halogen, $CF_3$, CN, lower-alkyl and/or lower-alkoxy.

In detail, the present invention relates to compounds of formula (I)

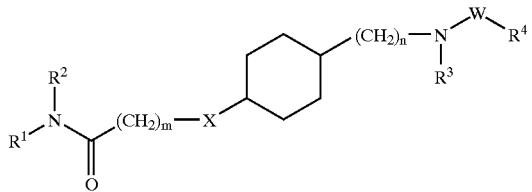

(I)

wherein $R^1$ is hydrogen or lower-alkyl;

$R^2$ is selected from hydroxy-lower-alkyl, hydroxy-lower-alkyl substituted with lower-alkyl, hydroxy-cycloalkyl, hydroxy-cycloalkyl substituted with lower-alkyl, carbamoyl-lower-alkyl and carbamoyl-lower alkyl substituted with lower-alkyl; or $R^1$ and $R^2$ are bonded to each other to form a ring together with the nitrogen atom to which they are attached and —$R^1$—$R^2$— is lower-alkylene which is substituted with a group selected from hydroxy, hydroxy-lower-alky and carbamoyl;

$R^3$ is hydrogen or lower-alkyl;

$R^4$ is aryl;

W is selected from CO, COO, CONR$^5$, CSO, CSNR$^5$, $SO_2$, and $SO_2NR^5$;

$R^5$ is hydrogen or lower-alkyl;

X is selected from a single bond, O, —CH═CH—, and —C≡C—;

m is 0, 1, 2, 3 or 4, wherein m is not 0 if X is O;

n is 0, 1, 2 or 3, wherein m+n is not more than 5.

Compounds of formula (I) as described above, in which X is a single bond or O, relate to a preferred embodiment of the present invention. The single bond and O are also individually preferred.

In a further preferred embodiment of the present invention, m is 0, 1 or 2, more preferably m is 0 or 2. 0 or 2 are also individually preferred. Compounds of formula (I), in which n is 0, 1 or 2 are also preferred, with those compounds wherein n is 0 or 2 being more preferred. 0 or 2 are also individually preferred. Compounds as described above, in which W is COO or $SO_2$, are also preferred, with COO and $SO_2$ individually being particularly preferred.

Other preferred compounds of the present invention are those in which $R^1$ represents lower-alkyl, preferably those in which $R^1$ is methyl. Another group of preferred compounds of the present invention are those in which $R^2$ represents hydroxy-lower-alkyl or carbamoyl-lower-alkyl optionally substituted with lower-alkyl, with those compounds wherein $R^2$ represents 3-hydroxy-propyl, 2-carbamoyl-ethyl or 2-methylcarbamoyl-ethyl being especially preferred.

Highly preferred is where $R^2$ represents 3-hydroxy-propyl.

Compounds of formula (I), wherein $R^1$ and $R^2$ are bonded to each other to form a ring together with the nitrogen atom to which they are attached and —$R^1$—$R^2$— is lower-alkylene which is substituted with hydroxy, hydroxy-lower-alkyl or carbamoyl are also preferred, with those compounds, wherein —$R^1$—$R^2$— is —$CH_2$—$CH_2$—CHOH—$CH_2$—$CH_2$— or —$CH_2$—$CH_2$—CH($CH_2$OH)—$CH_2$—$CH_2$— being especially preferred.

A further preferred embodiment of the present invention relates to compounds of formula (I), wherein $R^3$ represents lower-alkyl, particularly methyl.

Compounds of formula (I), wherein $R^4$ is phenyl substituted with halogen or $CF_3$ also relate to a preferred embodiment of the present invention, with those compounds, wherein $R^4$ is 4-chloro-phenyl or 4-trifluoromethyl-phenyl relating to a particularly preferred embodiment.

Accordingly, one embodiment in this invention relates to a compound of formula I wherein $R^1$ and $R^2$ are bonded to each other to form a ring together with the nitrogen atom to which they are attached and —$R^1$—$R^2$— is lower-alkylene which is substituted with hydroxy; $R^3$ is lower-alkyl; $R^4$ is aryl; and W is $SO_2$.

Another embodiment in this invention relates to a compound of formula I wherein $R^1$ is lower-alkyl; $R^2$ is hydroxy-cycloalkyl, $R^3$ is lower-alkyl; $R^4$ is aryl; and W is $SO_2$.

Another embodiment in this invention relates to a compound of formula I wherein $R^1$ is lower-alkyl; $R^2$ is hydroxy-lower-alkyl; $R^3$ is lower-alkyl; $R^4$ is aryl; and W is $SO_2$.

Another embodiment in this invention relates to a compound of formula I wherein $R^1$ is hydrogen; $R^2$ is hydroxy-lower-alkyl; $R^3$ is lower-alkyl; $R^4$ is aryl; and W is $SO_2$.

Another embodiment in this invention relates to a compound of formula I wherein $R^1$ is lower-alkyl; $R^2$ is hydroxy-lower-alkyl; $R^3$ is lower-alkyl; $R^4$ is aryl; and W is COO.

Another embodiment in this invention relates to a compound of formula I wherein $R^1$ is lower-alkyl; $R^2$ is hydroxy-lower-alkyl; $R^3$ is lower-alkyl; $R^4$ is aryl; and W is $SO_2$.

Another embodiment in this invention relates to a compound of formula I wherein $R^1$ and $R^2$ are bonded to each other to form a ring together with the nitrogen atom to which they are attached and —$R^1$—$R^2$— is lower-alkylene which is substituted with hydroxy; $R^3$ is lower alkyl; $R^4$ is aryl; and W is COO.

Another embodiment in this invention relates to a compound of formula I wherein $R^1$ is lower-alkyl; $R^2$ is carbamoyl substituted with lower alkyl; $R^3$ is lower-alkyl; $R^4$ is aryl; and W is COO.

Another embodiment in this invention relates to a compound of formula I wherein $R^1$ and $R^2$ are bonded to each other to form a ring together with the nitrogen atom to which they are attached and —$R^1$—$R^2$— is lower-alkylene which is substituted with carbamoyl; $R^3$ is lower-alkyl; $R^4$ is aryl; and W is COO.

Preferred compounds of formula (I) are those selected from the group consisting of trans-N-{4-[3-(4-Hydroxy-piperidin-1-yl)-3-oxo-propoxy]-cyclohexyl}-N-methyl-4-trifluoromethyl-benzenesulfonamide, trans-N-{4-[3-(4-Hydroxymethyl-piperidin-1-yl)-3-oxo-propoxy]-cyclohexyl}-N-methyl-4-trifluoromethyl-benzenesulfonamide, trans,-trans-N-(4-Hydroxy-cyclohexyl)-N-methyl-3-{4-[methyl-(4-trifluoromethyl-benzenesulfonyl)-amino]-cyclohexyloxy}-propionamide, trans-N-(2-hydroxy-ethyl)-N-methyl-3-{4-[methyl-(4-trifluoromethyl-benzenesulfonyl)-amino]-cyclohexyloxy}-propionamide, trans-N-(2-Hydroxy-ethyl)-3-{4-[methyl-(4-trifluoromethyl-benzenesulfonyl)-amino]-cyclohexyloxy}-propionamide, trans-N-Ethyl-N-(2-hydroxy-ethyl)-3-{4-[methyl-(4-trifluoromethyl-benzenesulfonyl)-amino]-cyclohexyloxy}-propionamide, trans-N-(2-Hydroxy-1-methyl-ethyl)-3-{4-[methyl-(4-trifluoromethyl-benzenesulfonyl)-amino]-cyclohexyloxy}-propionamide, trans-N-(3-Hydroxy-propyl)-N-methyl-3-{4-[methyl-(4-trifluoromethyl-benzenesulfonyl)-amino]-cyclohexyloxy}-propionamide, trans-N-(3-Hydroxy-propyl)-3-{4-[methyl-(4-trifluoromethyl-benzenesulfonyl)-amino]-cyclohexyloxy}-propionamide, and trans-3-{4-[(4-Bromo-benzenesulfonyl)-methyl-amino]-cyclohexyloxy}-N-(3-hydroxy-propyl)-N-methyl-propionamide.

Other preferred compounds of formula (I) are those selected from the group consisting of trans-3-{4-[(4-Chloro-benzenesulfonyl)-methyl-amino]-cyclohexyloxy}-N-(3-hydroxy-propyl)-N-methyl-propionamide, trans-(4-{2-[(3-Hydroxy-propyl)-methyl-carbamoyl]-ethoxy}-cyclohexyl)-methyl-carbamic acid 4-chloro-phenyl ester, trans-(4-{2-[(3-Hydroxy-propyl)-methyl-carbamoyl]-ethoxy}-cyclohexyl)-methyl-carbamic acid 4-bromo-phenyl ester, trans-(4-{2-[(3-Hydroxy-propyl)-methyl-carbamoyl]-ethoxy}-cyclohexyl)-methyl-carbamic acid 4-trifluoromethyl-phenyl ester, trans-(4-{2-[(2-Hydroxy-ethyl)-methyl-carbamoyl]-ethoxy}-cyclohexyl)-methyl-carbamic acid 4-bromo-phenyl ester, trans-(4-{2-[(2-Hydroxy-ethyl)-methyl-carbamoyl]-ethoxy}-cyclohexyl)-methyl-carbamic acid 4-fluoro-phenyl ester, trans-(4-{2-[(2-Hydroxy-ethyl)-methyl-carbamoyl]-ethoxy}-cyclohexyl)-methyl-carbamic acid 4-chloro-phenyl ester, trans-(4-{2-[(2-Hydroxy-ethyl)-methyl-carbamoyl]-ethoxy}-cyclohexyl)-methyl-carbamic acid 4-trifluoromethyl-phenyl ester, trans-3-{4-[(4-Bromo-benzenesulfonyl)-methyl-amino]-cyclohexyloxy}-N-(2-hydroxy-ethyl)-N-methyl-propionamide, and trans-3-{4-[(4-Chloro-benzenesulfonyl)-methyl-amino]-cyclohexyloxy}-N-(2-hydroxy-ethyl)-N-methyl-propionamide.

Other preferred compounds of formula (I) are those selected from the group consisting of trans (4-{[(3-Hydroxy-propyl)-methyl-carbamoyl]-methoxy}-cyclohexyl)-methyl-carbamic acid 4-chloro-phenyl ester, trans-(4-{[(3-Hydroxy-propyl)-methyl-carbamoyl]-methoxy}-cyclohexyl)-methyl-carbamic acid 4-trifluoromethyl-phenyl ester, trans-2-{4-[(4-Bromo-benzenesulfonyl)-methyl-amino]-cyclohexyloxy}-N-(3-hydroxy-propyl)-N-methyl-acetamide, trans-N-(3-Hydroxy-propyl)-N-methyl-2-{4-[methyl-(4-trifluoromethyl-benzenesulfonyl)-amino]-cyclohexyloxy}-acetamide, trans-{4-[(3-Hydroxy-propyl)-methyl-carbamoyl]-cyclohexylmethyl}-methyl-carbamic acid 4-chloro-phenyl ester, trans-(2-{4-[(3-Hydroxy-propyl)-methyl-carbamoyl]-cyclohexyl}-ethyl)-methyl-carbamic acid 4-chloro-phenyl ester, trans-(2-{4-[(2-Hydroxy-ethyl)-methyl-carbamoyl]-cyclohexyl}-ethyl)-methyl-carbamic acid 4-chloro-phenyl ester, trans-{2-[4-(4-Hydroxy-piperidine-1-carbonyl)-cyclohexyl]-ethyl}-methyl-carbamic acid 4-chloro-phenyl ester, trans-[2-(4-{[(2-Hydroxy-ethyl)-methyl-carbamoyl]-methyl}-cyclohexyl)-ethyl]-methyl-carbamic acid 4-chloro-phenyl ester, and trans-[2-(4-{[(3-hydroxy-propyl)-methyl-carbamoyl]-methyl}-cyclohexyl)-ethyl]-methyl-carbamic acid 4-chloro-phenyl ester.

Other preferred compounds of formula (I) are those selected from the group consisting of trans-Methyl-(2-{4-[methyl-(2-methylcarbamoyl-ethyl)-carbamoyl]-cyclohexyl}-ethyl)-carbamic acid 4-chloro-phenyl ester, trans-(2-{4-[(2-Carbamoyl-ethyl)-methyl-carbamoyl]-cyclohexyl}-ethyl)-methyl-carbamic acid 4-chloro-phenyl ester, trans-{2-[4-(Carbamoylmethyl-methyl-carbamoyl)-cyclohexyl]-ethyl}-methyl-carbamic acid 4-chloro-phenyl ester, and trans {2-[4-(4-Carbamoyl-piperidine-1-carbonyl)-cyclohexyl]-ethyl}-methyl-carbamic acid 4-chloro-phenyl ester.

Particularly preferred compounds of formula (I) are those selected from the group consisting of trans-N-{4-[3-(4-Hydroxy-piperidin-1-yl)-3-oxo-propoxy]-cyclohexyl}-N-methyl-4-trifluoromethyl-benzenesulfonamide, trans-N-{4-[3-(4-Hydroxymethyl-piperidin-1-yl)-3-oxo-propoxy]-cyclohexyl}-N-methyl-4-trifluoromethyl-benzenesulfonamide, trans-N-(3-Hydroxy-propyl)-N-methyl-3-{4-[methyl-(4-trifluoromethyl-benzenesulfonyl)-amino]-cyclohexyloxy}-propionamide, trans-(2-{4-[(3-Hydroxy-propyl)-methyl-carbamoyl]-cyclohexyl}-ethyl)-methyl-carbamic acid 4-chloro-phenyl ester, trans-{2-[4-(4-Hydroxy-piperidine-1-carbonyl)-cyclohexyl]-ethyl}-methyl-carbamic acid 4-chloro-phenyl ester, trans-Methyl-(2-{4-[methyl-(2-methylcarbamoyl-ethyl)-carbamoyl]-cyclohexyl}-ethyl)-carbamic acid 4-chlorophenyl ester, and trans-(2-{4-[(2-Carbamoyl-ethyl)-methyl-carbamoyl]-cyclohexyl}-ethyl)-methyl-carbamic acid 4-chlorophenyl ester.

Compounds of formula (I) can have one or more asymmetric carbon atoms and can exist in the form of optically pure enantiomers or as racemats. They can exist as cis- or trans-isomers.

The invention embraces all of these forms. Compounds of formula (I) which are trans-isomers (with reference to the cyclohexyl ring) are preferred.

It will be appreciated, that the compounds of general formula (I) in this invention may be derivatized at functional groups to provide derivatives which are capable of conversion back to the parent compound in vivo.

The present invention also relates to a process for the manufacture of compounds as described above, which process comprises (a) reacting a compound of formula (II)

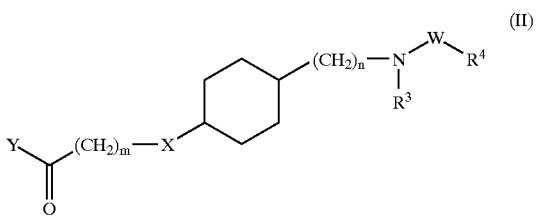

wherein $R^3$, $R^4$, X, W, m and n have the significances given above and Y is OH, Cl or Br, with a compound $NHR^1R^2$, wherein $R^1$ and $R^2$ have the significances given above, or (b) reacting a compound of formula (III)

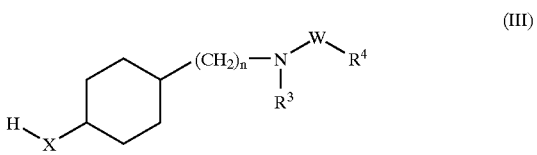

wherein $R^3$, $R^4$, W, and n have the significances given above and X=O, with a compound $R^1R^2N(C=O)$—$(CH_2)_m$—M, wherein M is hydroxy, mesylate, tosylate, triflate, Cl, Br or I, and $R^1$, $R^2$ and m have the significance given above.

Reactions of a compound of formula (II) with a compound $NHR^1R^2$ can be carried out by procedures known in the art, as described in the examples and as described in scheme 3 (step f) with EDCI, HOBT or BOP and a base such as Huenig's base, $NEt_3$ or NMM in $CH_2Cl_2$, DMF, DMA or dioxane. Reactions of a compound of formula (III) with a compound $R^1R^2N(C=O)$—$(CH_2)_m$—M can be carried out by procedures known in the art, as described in the examples and as described in scheme 2 (step d) for M=mesylate, tosylate, Cl, Br or I with NaOH, $nBu_4NHSO_4$ preferentially in solvents like toluene or $CH_2Cl_2$ or alternatively for compounds with M=OH via the in-situ preparation of the triflates with trifluoromethane sulfonic anhydride/2,6-ditert-butylpyridine preferentially in solvents like $CH_2Cl_2$ or nitromethane.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of pharmaceutical compositions for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such pharmaceutical compositions comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

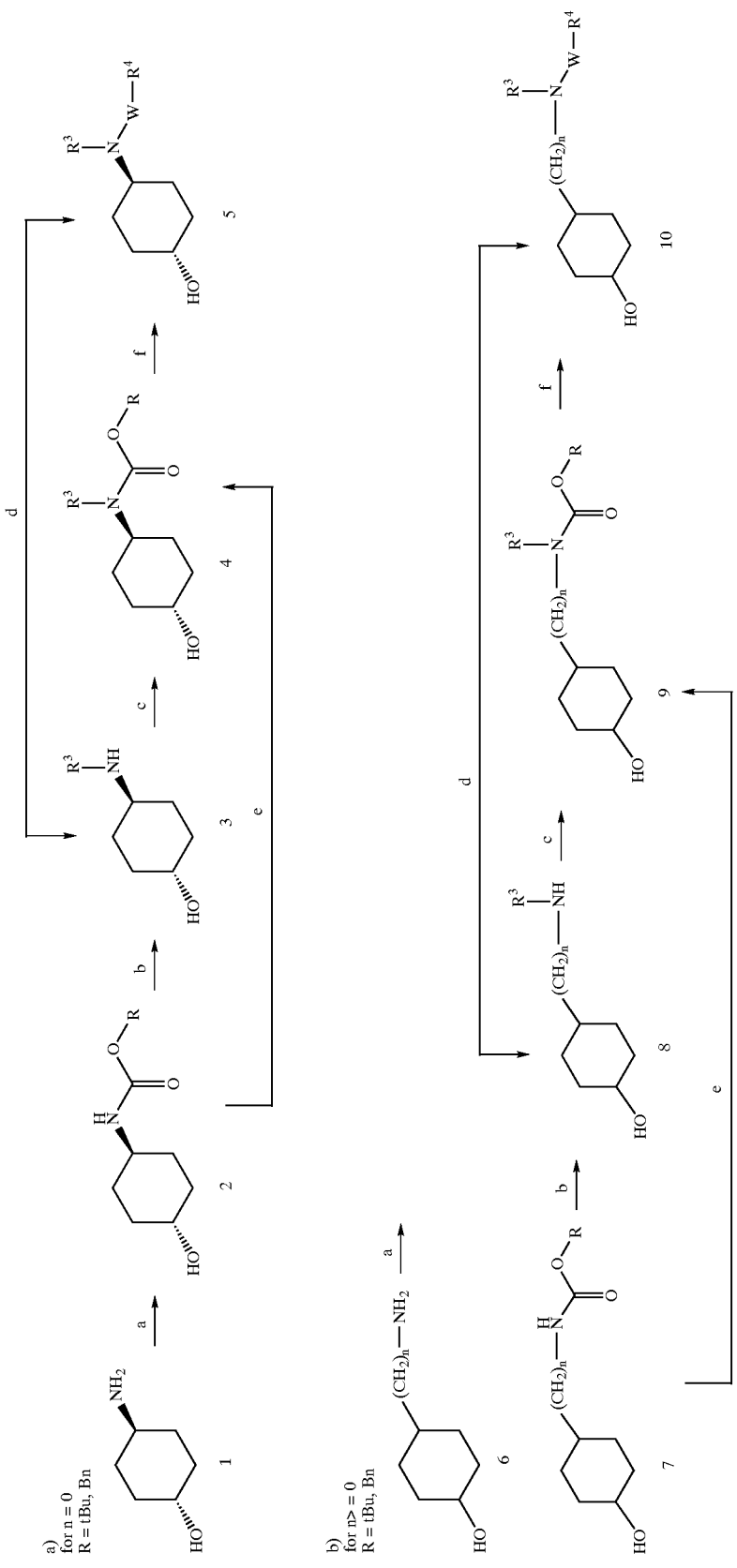

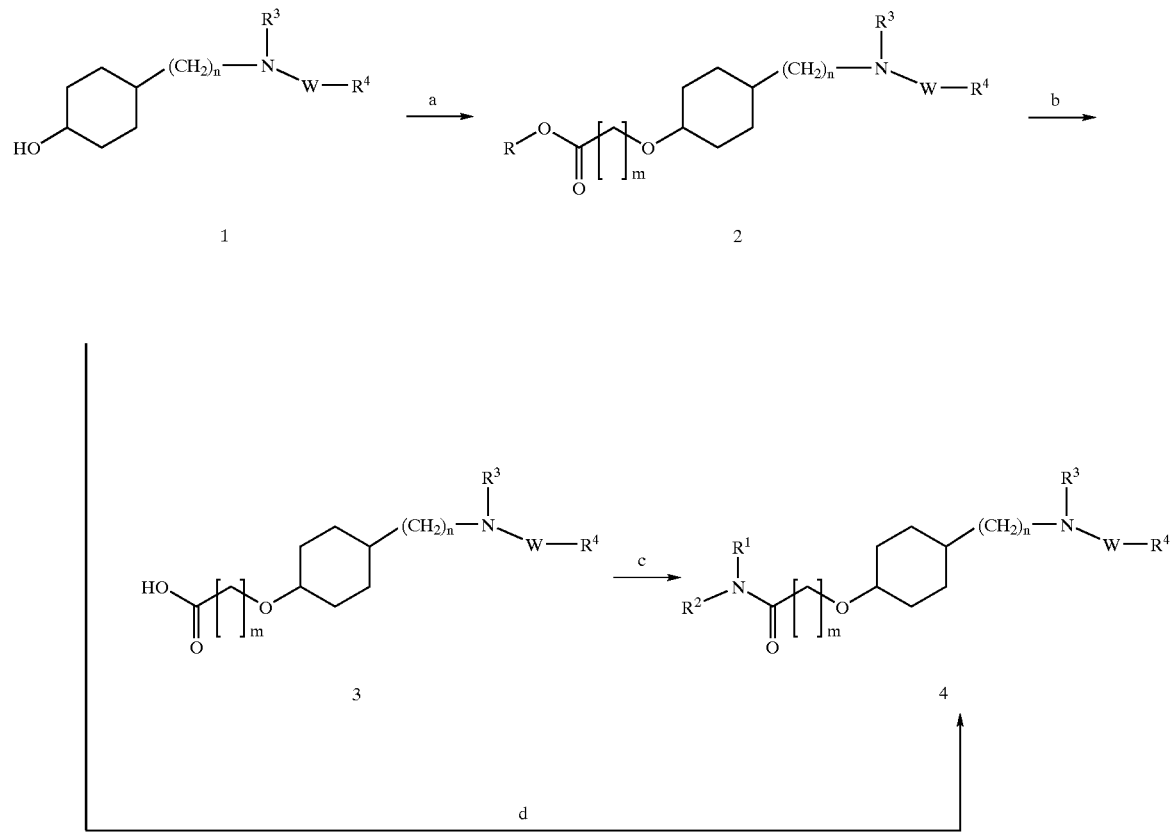

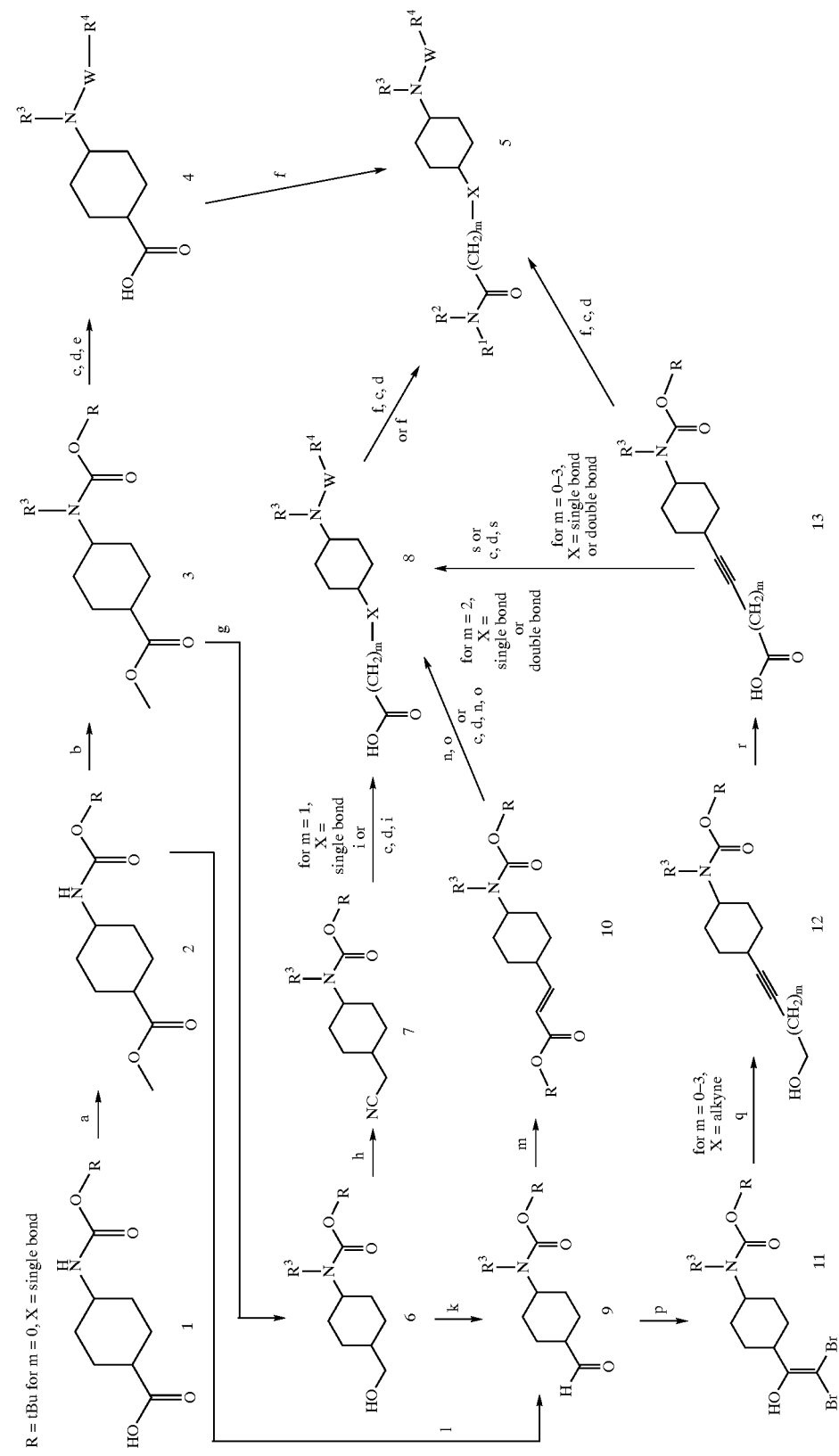
Scheme 3

Scheme 4
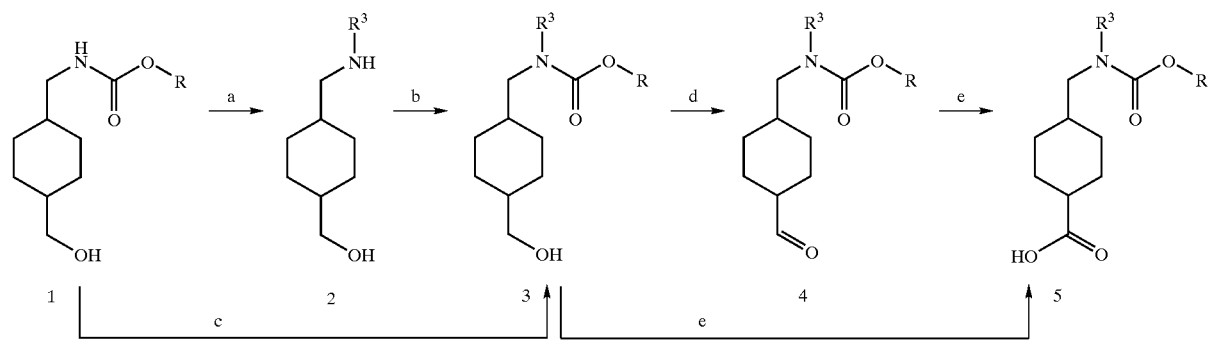
R = tBu
Scheme 5
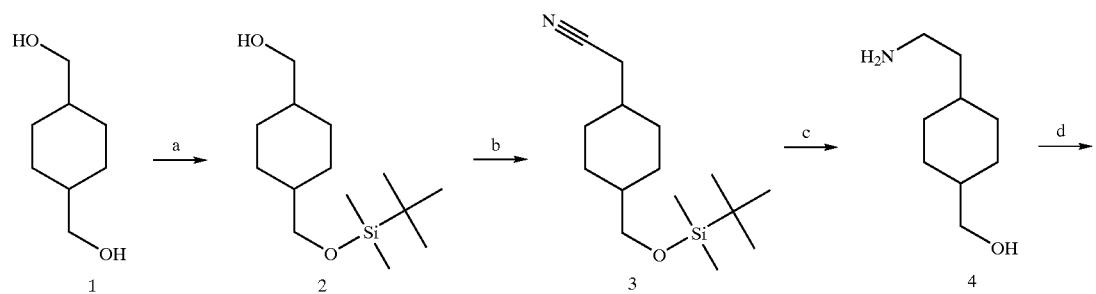
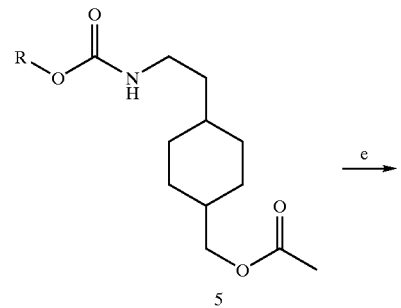
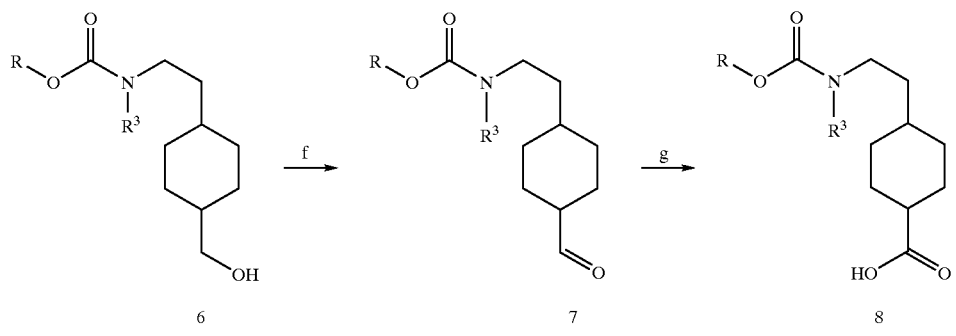
R = tBu

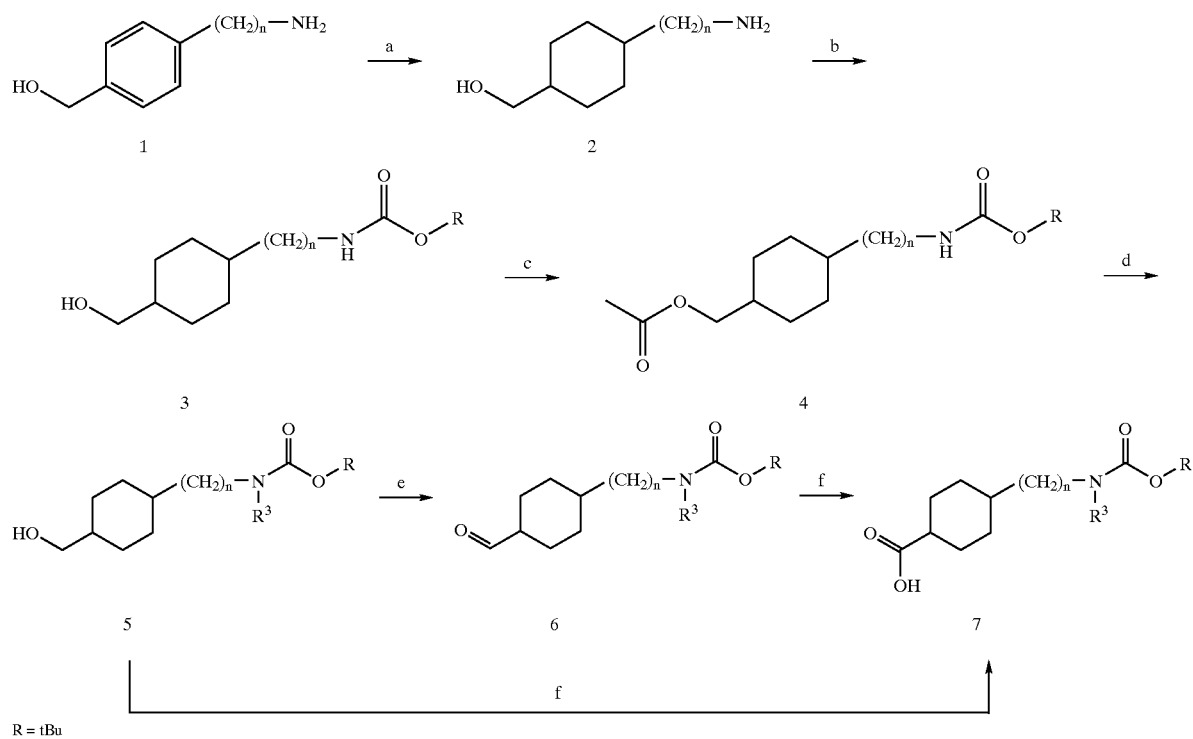
Scheme 6
R = tBu
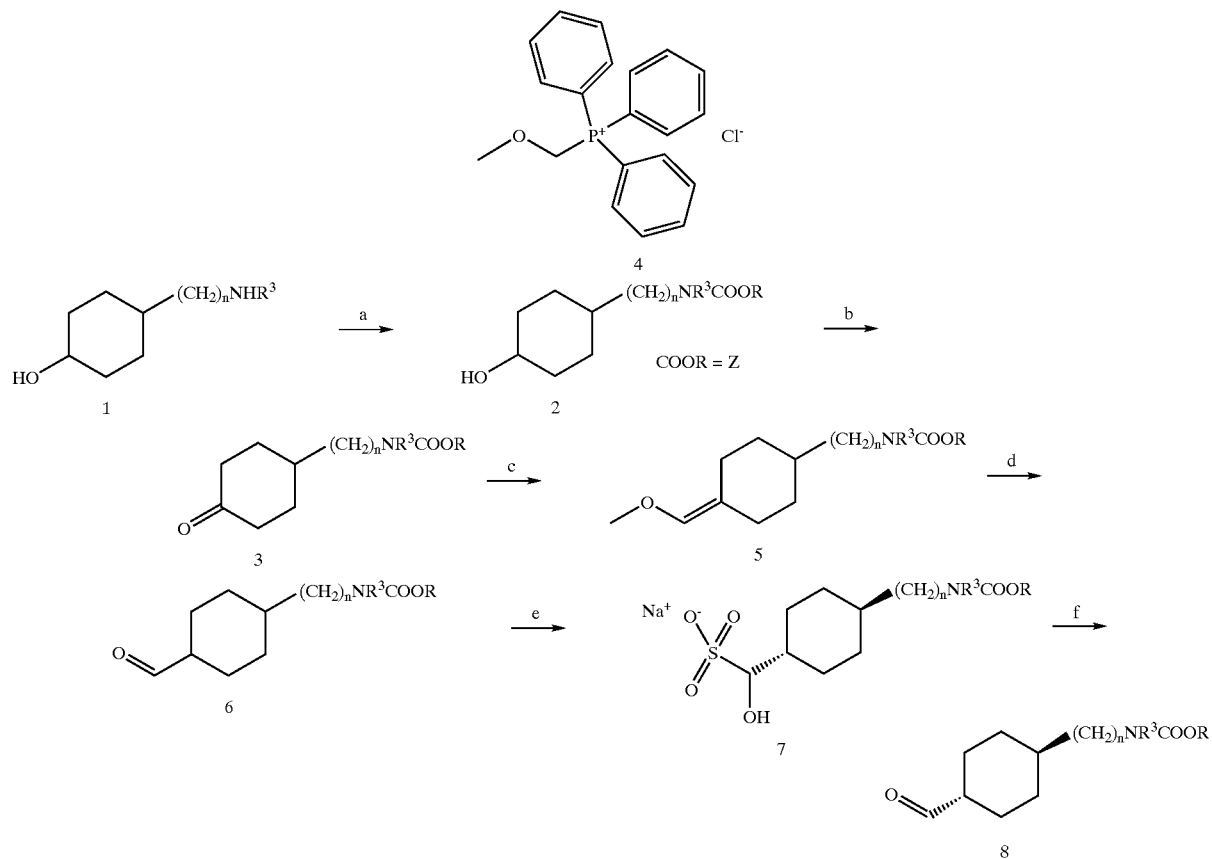
Scheme 7
COOR = Z

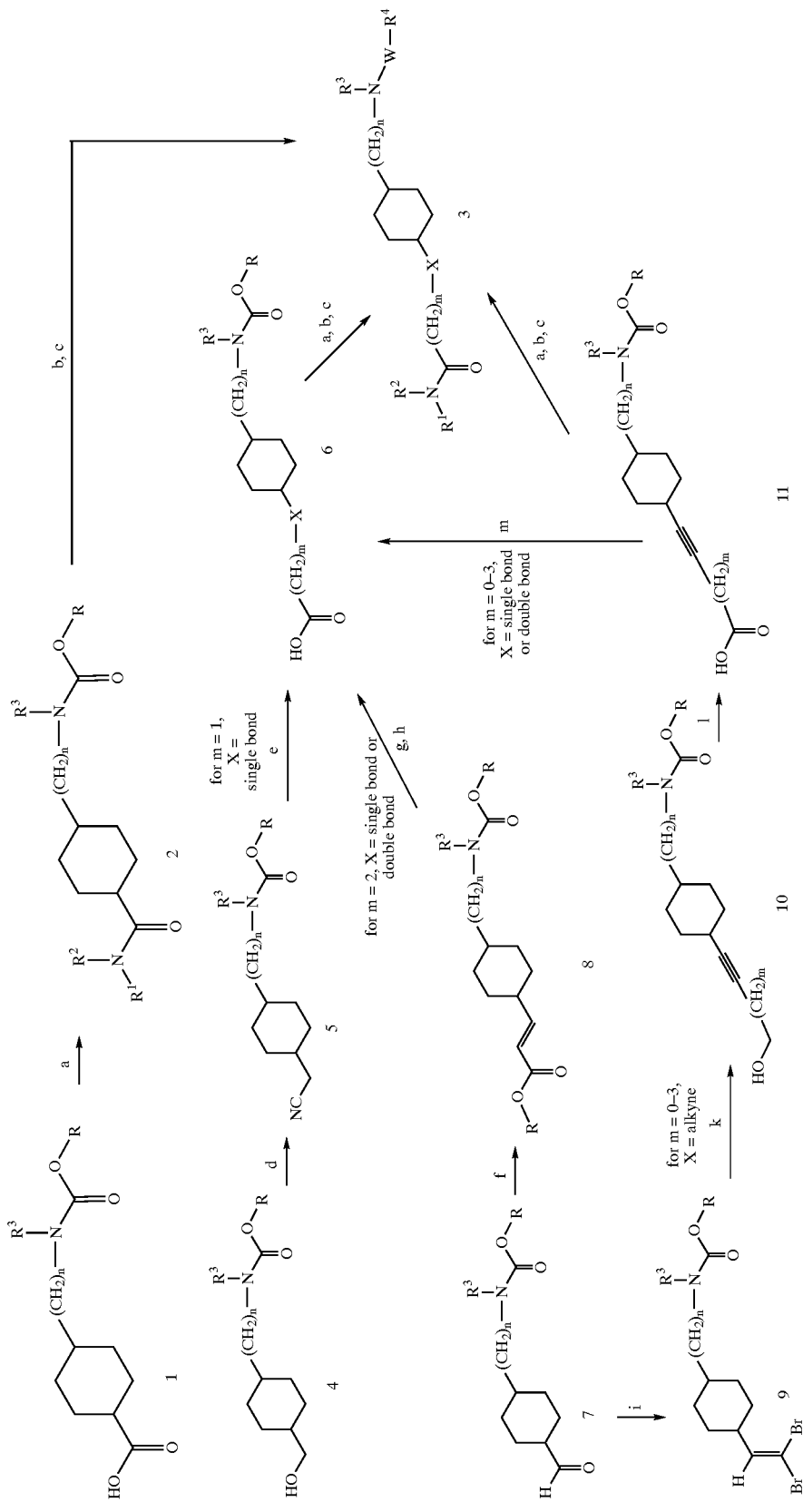

Scheme 1

The preparation of the starting materials for aminocyclohexyl derivatives of formula (I) in which X is O is depicted in scheme 1. For compounds with n=0, the synthesis starts from trans-4-aminocyclohexanol 1 which is converted to the Z-derivative or the BOC derivative 2 e.g. ZCl, $Na_2CO_3$, THF, $H_2O$ or $(BOC)_2O$, iPrOH, $CH_2Cl_2$, respectively (step a). Lithium aluminum hydride reduction yields trans-4-methylaminocyclohexanol 3 which is either BOC-protected to yield compound 4 (step c) or is directly transferred (step d) into the desired $R^4W$-derivative 5 using one of the methods described later for compound 4 in scheme 2. If needed, the aminocyclohexanol derivative can be treated with hexamethyldisilazane at reflux, prior to the introduction of the $R^4W$-moiety. Alternatively, the residue $R^3$ can be introduced via alkylation. Therefore, compound 2 can be first O-protected and then N-alkylated at the protected amino function with an alkyl derivative in the presence of a base like sodium hydride in a solvent like N,N-dimethylformamide, THF or acetonitrile at temperatures between room temperature (hereinafter: RT) and 80° C.; after O-deprotection the compound 3 is obtained (step e). BOC-deprotection (TFA, $CH_2Cl_2$) or Z-deprotection (hydrogenation) followed by treatment with $R^4W$-derivatives gives compounds of the formula 5 (step f).

For n>0 (scheme 1b), the aminocyclohexanol derivatives may be derived from the corresponding aminophenol, 4-hydroxybenzylamine, tyramine or 3-(4-hydroxyphenyl)propylamine by hydrogenation. These derivatives may be converted to the compounds of formula 10 as described for 5.

Scheme 2

The synthesis of ether derivatives of formula (I) is depicted in scheme 2. The amino-cyclohexanol derivative 1 can be treated under phase transfer conditions with e.g. ω-halo-alkylcarbonic acid tert butlyl esters, NaOH, $nBu_4NHSO_4$ to yield ester 2. Alternatively, the preparation via the in situ generated triflate is possible. From the corresponding ω-hydroxyalkylcarbonic acid alkyl esters the triflates may be formed with trifluoromethane sulfonic anhydride/2,6-di-tert-butylpyridine in $CH_2Cl_2$ at 0° C. These are then reacted with alcohol 1 with 2,6-di-tert-butylpyridine as a base in nitromethane at 60° C. to yield ester 2 [following a procedure of Belostotskii and Hassner, Tetrahedron Lett. 35:5075–5076 (1994)]. (step a).

Saponification of the ester 2 using standard conditions e.g. LiOH or NaOH in EtOH, MeOH or THF for the alkyl esters or TFA or HCl in THF, ether or $CH_2Cl_2$ for tert butyl esters give the acid 3 (step b). Treatment of the acid 3 with $NHR^1R^2$, EDCI, HOBT or $NHR^1R^2$, BOP and a base such as Huenig's base, $NEt_3$ or NMM in $CH_2Cl_2$, DMF, DMA or dioxane gives amide 4 (step c). Alternatively a two-step procedure might be used: treatment of the acid 2 with oxalyl chloride in $CH_2Cl_2$ in the presence of DMF, followed by reaction with the corresponding amine $NHR^1R^2$.

The amino-cyclohexanol derivative 1 can be treated under phase transfer conditions with the appropriate ω-halo-alkylcarbonic acid amide, NaOH, $nBu_4NHSO_4$ to yield ester 4 directly (step d). Alternatively, the preparation via the in situ generated triflate is possible. From the corresponding ω-hydroxyalkylcarbonic acid amide, the triflates may be formed with trifluoromethane sulfonic anhydride/2,6-di-tert-butylpyridine in $CH_2Cl_2$ at 0° C. These are then reacted with alcohol 1 with 2,6-di-tert-butylpyridine as a base in nitromethane at 60° C. to yield ester 2 [following a procedure of Belostotskii and Hassner, Tetrahedron Lett. 35:5075–5076 (1994)]. (step d)

In the case that the reaction was performed with an amine $NHR^1R^{2'}$ in which $R^{2'}$ contains an ester moiety this can be reduced by e.g. $NaBH_4$ in solvents like THF or MeOH to the corresponding hydroxyalkyl derivatives. Furthermore, the ester moiety may be saponified as described above and the acid may be transferred into the carbamoyl lower alkyl derivative by treatment of the acid with oxalyl chloride in $CH_2Cl_2$ in the presence of DMF, followed by reaction with alkylamine or ammonia.

If $R^4W$ in 4 is a protecting moiety, this can be cleaved using TFA in $CH_2Cl_2$ for BOC-groups or by hydrogenation in methanol/HCl with Pd/C for Z-groups. The resulting ammonium salt may be treated according to one of the procedures described to derive the appropriate $R^4W$ derivative 4. If needed, the aminocyclohexane derivative can be treated with hexamethyldisilazane at reflux, prior to the introduction of the $R^4W$-moiety.

Sulfonamides: Sulfonylation of the amines is done in dioxane or $CH_2Cl_2$ with Huenig's base and a sulfonyl chloride over night at RT to yield the sulfonamide 4.

Carbamates: The amines may be reacted with $R^4OCOCl$/Huenig's base in dioxane or $CH_2Cl_2$. Alternatively, the chloroformates may be prepared in situ by treatment of $R^4OH$ with $Cl_3COCl$ in the presence of quinoline followed by reaction with the amines in the presence of Huenig's base.

Thiocarbamates: The amines may be reacted with $R^4OCSCl$ in dioxane.

Ureas: The amines may be reacted with isocyanate in dioxane at RT.

Thioureas: The amines may be reacted with isothiocyanate in dioxane at RT.

Amides: The amines may be reacted with $R^4COCl$/Huenig's base in $CH_2Cl_2$, $R^4COOH$/EDCI/DMAP (via formation of the symmetrical anhydride, and subsequent addition of the starting amine at –10° C. to RT) or alternatively with $R^4COOH$/EDCI/DMAP or $R^4COOH$/Huenig's base or NMM/EDCI/HOBT in DMF, dioxane or $CH_2Cl_2$ at RT.

Sulfamides: The amines may be reacted with sulfamoyl chlorides in dioxane in the presence of an excess of triethylamine to yield sulfamide 3 or 5. The sulfamoyl chlorides can be prepared from $R^4NH_2$ and chlorosulfonic acid in $CH_2Cl_2$ at 0° C. to RT followed by reaction with $PCl_5$ in toluene at 75° C. Alternatively, the sulfamoyl chlorides can be synthesized in acetonitrile with $R^4NH_2$ and sulfuryl chloride at 0° C. to 65° C.

Scheme 3

In scheme 3, the synthesis of carbon analogues is depicted. For compounds with n=0, m=0 and X=single bond, the synthesis starts from 4-tert-butoxycarbonyl amino-cyclohexane-carboxylic acid 1. This is converted to the derivative 2 by ester formation (e.g. carbonyl-di-imidazole, methanol in THF, step a) and this is followed by direct alkylation using sodium hydride and a reactive alkyl derivative (step b). The ester 3 is BOC deprotected (TFA, $CH_2Cl_2$, step c), transferred into the desired $R^4W$-derivative using one of the methods described previously for compound 4 in scheme 2 (step d), and saponified using standard conditions e.g. LiOH or NaOH in EtOH, MeOH or THF for the alkyl esters or TFA or HCl in THF, ether or $CH_2Cl_2$ for tert butyl esters to give the acid 4 (step e).

Treatment of the acid 4 with $NHR^1R^2$, EDCI, HOBT or $NHR^1R^2$, BOP and a base such as Huenig's base, $NEt_3$ or NMM in $CH_2Cl_2$, DMF, DMA or dioxane gives the amide 5. Alternatively a two-step procedure might be used: treatment of the acid 4 with oxalyl chloride in $CH_2Cl_2$ in the presence of DMF, followed by reaction with the corresponding amine $NHR^1R^2$.

In the case that the reaction was performed with an amine $NHR^1R^{2'}$ in which $R^{2'}$ contains an ester moiety this can be reduced by e.g. $NaBH_4$ in solvents like THF, MeOH to the corresponding hydroxyalkyl derivatives. Furthermore, the ester moiety may be saponified as described above and the acid may be transferred into the carbamoyl lower alkyl derivative by treatment of the acid with oxalyl chloride in $CH_2Cl_2$ in the presence of DMF, followed by reaction with alkylamine or ammonia.

Alternatively, the BOC protected ester 3 can be transferred into the desired amide before introducing the appropriate residue $R^4W$.

For n=0, m=1, X=single bond, reduction of the ester 3 with lithium aluminum hydride yields the protected alcohol 6 (step g). Reaction of 6 with e.g. methanesulfonyl chloride in dichloromethane and triethylamine gives the corresponding methanesulfonate, which may be treated with sodium cyanide in N,N-dimethylformamide at 80° C. to yield the cyano compound 7 (step h). Reduction of the cyano compound 7 with DIBAH (−78° C. to RT in THF) gives the C1-elongated aldyhyde which can be oxidized to the desired carboxylic acid 8 using ruthenium (III) chloride-hydrate, sodium metaperiodate in a mixture of $CCl_4$, water and acetonitrile (step i).

The conversion of acid 8 to the final product 5 may be achieved as described previously for compound 4 (step f). The introduction of the appropriate $WR^4$ residue may be accomplished via the procedures described in c and d either at the nitrile stage (compound 7) or after amide formation.

For $C_2$-elongation: Swern oxidation of the alcohol 6 gives the corresponding aldehyde 9. Alternatively, the aldehyde 9 maybe prepared via the Weinreb-amide starting from ester 3 (saponification of the ester using LiOH or NaOH in EtOH, MeOH or THF, followed by treatment with N,O-dimethyl-hydroxyl-amine-hydrochloride with EDCI and HOBT in $CH_2Cl_2$ at RT and reduction by lithium aluminum hydride, step l). Horner-Emmons reaction with triethyl phosphono acetate, sodium methanolate or sodium ethanolate in ethanol gives the unsaturated ester 10 (step m). The ester can be saponified employing standard conditions (e.g. LiOH or NaOH in EtOH, MeOH or THF) to give the acid 8 (step o, X=double bond) or can be hydrogenated in the presence of 10% palladium on carbon in methanol prior to saponification of the ester to give acid 8 (steps n,o, X=single bond). Acid 8 can then be converted to the final product 5 as described above (step f). The introduction of the appropriate $WR^4$ residue maybe accomplished via the procedures described in c and d either at the ester stage (compound 10) or after amide formation.

For $C_2$ up to $C_m$-elongation, Corey-Fuchs methodology may be used: Therefore, the aldehyde 9 can be treated with triphenylphosphine, tetrabromomethane and triethylamine in $CH_2Cl_2$ at 0° C. to RT to yield 2,2-dibromo-vinyl derivative 11 (step p). Rearrangement with n-BuLi (ca 1.6 M in hexane) in THF at −78° C., followed by reaction with formaldehyde (−78° C. to RT) gives the propargyl alcohol 12 (m=0) [step q, following conditions described in Marshall et al., J. Org. Chem. 61:5729–5735 (1996); and Baker et al., J. Chem. Soc. Perkin Trans. 1:1415–1421 (1990)]. Acid 8 can then be converted to the final product 5 as described above (step f).

For longer side chains, the rearrangement is performed with n-BuLi (ca 1.6 M in hexane) in THF at −78° C. as described above. This is followed by addition of a cosolvents such as DMPU and reaction of the intermediate with O-protected 1-bromo-alcohols (step q; e.g. 1-bromo-n-tetrahydropyaranyloxyalkane) to give the O-protected compounds which, after acidic hydrolysis, give the desired compounds 12 (m=1–3). Oxidation of the primary alcohol using e.g. Jones' reagent gives the acid 13. The acid 13 may be directly converted to the corresponding final products 5 using the procedures described above (step f). Alternatively, it might be converted to compound 8 in which X is a single bond by hydrogenation in the presence of Pt/C or in which X is CH=CH by hydrogenation with other known methods prior to amide formation (step f).

The introduction of the appropriate $WR^4$ residue may be accomplished via the procedures described in c and d either at the nitrile stage (compound 7) or after amide formation.

Scheme 4 to scheme 7 describe the synthesis of intermediates for compounds with n>0 and X=single bond, CH=CH or triple bond.

Scheme 4

In scheme 4, the preparation of cis- or trans-(4-methylaminomethyl-cyclohexyl)-methanol ($R^3$=Me) from cis- or trans-(4-hydroxymethyl-cyclohexylmethyl)-carbamic acid tert-butyl ester 1 [U.S. Pat. Nos. 5,843,973 or 6,022,969] by treatment with lithium aluminum hydride in tetrahydrofuran between RT and the reflux temperature of the tetrahydrofuran is described (step a). Introduction of a tert-butoxycarbonyl protective group by treatment with di-tert-butyl-dicarbonate in methanol/triethylamine between −10° C. and RT gives compound 3 ($A^5$=Me) (step b). Compound 1 can also be first O-protected and then N-alkylated at the tert-butoxycarbonyl protected amino group with an alkyl halide in the presence of a base like sodium hydride in a solvent like N,N-dimethylformamide, THF or acetonitrile at temperatures between RT and 80° C. to introduce substituents $R^3$; after O-deprotection the compound 3 is obtained (step c). Compound 3 is subsequently oxidized to the corresponding aldehyde 4 by using e.g. Swern conditions: oxalyl chloride/dimethylsulfoxide/triethylamine in dichloromethane, −78° C. to RT (step d). This aldehyde 4 can be oxidized to the desired carboxylic acid 5 using e.g. ruthenium (III) chloride-hydrate, sodium metaperiodate in a mixture of $CCl_4$, water and acetonitrile. Alternatively, the oxidation of compound 3 can be accomplished in one step using ruthenium (III) chloride-hydrate, sodium metaperiodate in a mixture of $CCl_4$, water and acetonitrile to give acid 5 (step e).

Scheme 5

In scheme 5, the preparation of cis or trans-[4-(tert-butyl-dimethyl-silanyloxymethyl)-cyclohexyl]-methanol 2 from the corresponding bis-hydroxymethyl cyclohexane derivatives 1 by treatment with one equivalent of n-butyl lithium in tetrahydrofuran at −78° C. followed by one equivalent of tert-butyl-dimethyl-chlorosilane at −65° C. to RT is described (step a). Mesylation of [4-(tert-butyl-dimethyl-silanyloxymethyl)-cyclohexyl]-methanol 2 (methanesulfonyl chloride in dichloromethane and triethylamine at 0–10° C.) gives the corresponding methanesulfonate, which is treated with sodium cyanide in N,N-dimethylformamide at 80° C. to give the cyano compound 3 (step b). Direct reduction of the cyano compound 3 e.g. by hydrogenation with a platinum catalyst in acidic methanol (e.g. in situ formation from $CHCl_3$ in MeOH) gives the primary O-deprotected amine 4 (step c). Treatment of the amino-alcohol 4 first with di-tert-butyl-dicarbonate in dichloromethane in the presence of triethylamine followed by acetic anhydride and pyridine in dichloromethane gives the di-protected compound 5 (step d). Compound 5 can be N-alkylated at the tert-butoxycarbonyl protected amino group with an alkyl halide in the presence of a base like sodium hydride in a solvent like N,N-dimethylformamide or acetonitrile at temperatures between RT and 80° C. to introduce substituents $R^3$ and gives, after basic cleavage of the acetate function, the primary hydroxy compound 6 (step e). The primary hydroxy compound 6 can be oxidized subsequently to the corresponding aldehyde 7 by using e.g. Swern conditions: oxalyl chloride/dimethylsulfoxide/ triethylamine in dichloromethane, −78° C. to RT (step f). This aldehyde 7 can be oxidized to the desired carboxylic acid 8 using e.g. ruthenium (III) chloride-hydrate, sodium metaperiodate in a mixture of $CCl_4$, water and acetonitrile (step g). Alternatively, the oxidation of compound 6 can be accomplished in one step using ruthenium (III) chloride-hydrate, sodium metaperiodate in a mixture of $CCl_4$, water and acetonitrile to give acid 8 (step g).

Scheme 6

Scheme 6 depicts an alternative route to aminocyclohexane derivatives 6 and 7. Compounds 2 may be derived from the corresponding 4-(aminomethyl)benzyl alcohol, 4-(2-aminoethyl)benzyl alcohol, 4-(3-aminopropyl)benzyl alcohol by hydrogenation (step a). Treatment of the amino-alcohol 2 first with di-tert-butyl-dicarbonate in dichloromethane in the presence of triethylamine (step b) followed by acetic anhydride and pyridine in dichloromethane gives the di-protected compound 4 (step c). Compound 4 can be N-alkylated at the tert-butoxycarbonyl protected amino group with an alkyl halide in the presence of a base like sodium hydride in a solvent like N,N-dimethylformamide or acetonitrile at temperatures between RT and 80° C. to introduce substituents $R^3$ and gives, after basic cleavage of the acetate function, the primary hydroxy compound 5 (step d). The primary hydroxy compound 5 can be oxidized subsequently to the corresponding aldehyde 6 by using e.g. Swern conditions: oxalyl chloride/dimethylsulfoxide/triethylamine in dichloromethane, −78° C. to RT (step e). This aldehyde 6 can be oxidized to the desired carboxylic acid 7 using e.g. ruthenium (III) chloride-hydrate, sodium metaperiodate in a mixture of $CCl_4$, water and acetonitrile (step f). Alternatively, the oxidation of compound 5 can be accomplished in one step using ruthenium (III) chloride-hydrate, sodium metaperiodate in a mixture of $CCl_4$, water and acetonitrile to give acid 7 (step f).

Scheme 7

Scheme 7 describes the synthesis of pure trans-aldehyde building block 8. Optionally $R^3$ substituted cyclohexanol 1 is synthesized by hydrogenation of the corresponding 4-aminophenol, 4-hydroxybenzylamine, tyramine or 3-(4-hydroxyphenyl)propylamine (see also scheme 1). Amine 1 is converted to the N-protected-derivative 2 (e.g. ZCl, $Na_2CO_3/THF/H_2O$) (step a). Oxidation with TEMPO (2,2,6,6-tetramethylpiperidine 1-oxyl, radical) and sodium hypochlorite gives ketone 3 (step b). Wittig reaction with (methoxymethyl)triphenylphosphonium chloride 4 in THF and potassium t-butoxide as base gives enolether 5 (step c). If $R^3$=H, modification of the residue is possible at this stage (with $R^3$-halogenide/NaH in DMF or DMA). Hydrolysis of enolether 5 with 1 N HCl in THF at reflux (step d) gives aldehyde 6. The crude aldehyde 6 (as a cis/trans mixture) can be isomerised via bisulfite-adduct 7 (with disodium pyrosulfite in water/TBME, step e). Bisulfite adduct 7 can then be converted to the pure trans-aldehyde 8 with aqueous $Na_2CO_3$ in water/TBME (step f).

Scheme 8

In scheme 8, the synthesis of carbon analogues is depicted. For compounds with n>0, m=0 and X=single bond, the synthesis starts from 4-tert-butoxycarbonyl aminoalkyl-cyclohexane-carboxylic acid 1 (see scheme 4-6 for preparation). This is converted to the amide 2 by treatment with $NHR^1R^2$, EDCI, HOBT or $NHR^1R^2$, BOP and a base such as Huenig's base, $NEt_3$, NMM in $CH_2Cl_2$, DMF, DMA or dioxane. Alternatively a two-step procedure might be used: treatment of the acid 1 with oxalyl chloride in $CH_2Cl_2$ in the presence of DMF, followed by reaction with the corresponding amine $NHR^1R^2$. In the case that the reaction was performed with an amine $NHR^1R^{2'}$ in which $R^{2'}$ contains an ester moiety this can be reduced by e.g. $NaBH_4$ in solvents like THF, MeOH to the corresponding hydroxy-alkyl derivatives. Furthermore, the ester moiety may be saponified as described above and the acid may be transferred into the carbamoyl lower alkyl derivative by treatment of the acid with oxalyl chloride in $CH_2Cl_2$ in the presence of DMF, followed by reaction with alkylamine or ammonia (step a). The amine moiety of the amide 2 is deprotected (for BOC: TFA, $CH_2Cl_2$, for Z: hydrogenation), and the amine transferred into the desired $R^4W$-derivative using one of the methods described previously for compound 4 in scheme 2 (step b,c).

Alternatively, the sequence of steps can be inverted, introduction of the desired $R^4W$- residue prior to amide formation. In this case, the acid moiety can be treated with hexamethyldisilazane at reflux prior to the introduction of the $R^4W$-moiety.

For n>0, m=1, X=single bond, the synthesis starts with the alcohol 4 (see scheme 4-6 for preparation). Reaction of 4 with e.g. methanesulfonyl chloride in dichloromethane and triethylamine gives the corresponding methanesulfonate, which may be treated with sodium cyanide in N,N-dimethylformamide at 80° C. to yield the cyano compound 5 (step d). Reduction of the cyano compound 5 with DIBAH (−78° C. to RT in THF) gives the Cl-elongated aldehyde which can be oxidized to the desired carboxylic acid 6 using ruthenium (III) chloride-hydrate, sodium metaperiodate in a mixture of $CCl_4$, water and acetonitrile (step e). The conversion of acid 6 to the final product 3 may be achieved as described previously (steps a,b,c).

For $C_2$-elongation, the aldehyde 7 (see scheme 4-6 for preparation) may be subjected to Horner-Emmons reaction with triethyl phosphono acetate, sodium methanolate in ethanol to give the unsaturated ester 8 (step f). The ester can be saponified employing standard conditions (e.g. conditions e.g. LiOH or NaOH in EtOH, MeOH or THF) to give the acid 6 (step g, X=double bond) or can be hydrogenated in the presence of 10% palladium on carbon in methanol prior to saponification of the ester to give acid 6 (steps g,h, X=single bond). Acid 6 may be converted to compound 3 as described above (steps a,b,c).

For $C_2$ up to $C_m$-elongation, Corey-Fuchs methodology may be used: Therefore, the aldehyde 7 can be treated with triphenylphosphine, tetrabromomethane and triethylamine in $CH_2Cl_2$ at 0° C. to RT to yield 2,2-dibromo-vinyl derivative 9 (step i). Rearrangement with n-BuLi (ca 1.6 M in hexane) in THF at −78° C., followed by reaction with formaldehyde (−78° C. to RT) gives the propargyl alcohol 10 (m=0) [step k, following conditions described in Marshall et al., J. Org. Chem. 61:5729–5735 (1996); and Baker et al., J. Chem. Soc. Perkin Trans. 1:1415–1421 (1990)].

For longer side chains, the rearrangement is performed with n-BuLi (ca 1.6 M in hexane) in THF at −78° C. as described above. This is followed by addition of a cosolvents such as DMPU and reaction of the intermediate with O-protected 1-bromo-alcohols (step q; e.g. 1-bromo-n-tetrahydropyaranyloxyalkane) to give the O-protected compounds which after acidic hydrolysis give the desired compounds 10 (m=1–3). Oxidation of the primary alcohol using e.g. Jones' reagent gives the acid 11. The acid 11 may be directly converted to the corresponding final products 3 using the procedures described above (step a,b,c). Alternatively, it might be converted to compounds 6 in which X is a single bond by hydrogenation in the presence of Pt/C or in which X is CH=CH by hydrogenation with other known methods prior to amide formation. The conversion of acid 6 to the final product 3 may be achieved as described previously (step a,b,c).

The following tests were carried out in order to determine the activity of the compounds of formula I and their salts. Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/$\mu$l with ethanol and mixed with phosphate buffer-1% BSA (bovine serum albumin). A stock solution of 1 mM test substance in DMSO was diluted to the desired concentration with phosphate buffer-1% BSA. 40 $\mu$l of microsomes were mixed with 20 $\mu$l of the solution of the test substance and the reaction was subsequently started with 20 $\mu$l of the [$^{14}$C]R,S-MOS solution. The final conditions were: 0.4 mg/ml of microsomal proteins and 30 $\mu$l of [$^{14}$C]R,S-MOS in phosphate buffer, pH 7.4, containing 0.5% albumin, DMSO <0.1% and ethanol <2%, in a total volume of 80 $\mu$l.

After 1 hour at 37° C. the reaction was stopped by the addition of 0.6 ml of 10 % KOH-methanol, 0.7 ml of water and 0.1 ml of hexane:ether (1:1, v/v) which contained 25 $\mu$g of non-radioactive MOS and 25 $\mu$g of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 $\mu$l of hexane:ether and applied to a silica gel plate. Chromatographic separation was effected in hexane:ether (1:1, v/v) as the eluent. The Rf values for the MOS substrate and the lanosterol product were 0.91 and 0.54, respectively. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the IC$_{50}$ value was calculated, i.e. the concentration required to reduce the conversion of MOS into lanosterol to 50% of the control value. The preferred compounds of the present invention exhibit IC$_{50}$ values of 1 nM to 10 $\mu$M, preferably of 1 nM to 500 nM.

The compounds of formula I and/or their pharmaceutically acceptable salts can be used as pharmaceutical compositions, e.g. in the form of pharmaceutical preparations for enteral, parenteral or topical administration. They can be administered, for example, per orally, e.g. in the form of tablets, coated tablets, dragées, hard and soft gelatin capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatine capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants are considered as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1 to 500 mg, preferably 1 to 100 mg, of a compound of formula I.

The following Examples serve to illustrate the present invention in more detail. They are, however, not intended to limit its scope in any manner.

EXAMPLES

Abbreviations used: BOC=t-butyloxycarbonyl, BOP=benzotriazol-1-yloxytris(dimethylamino)phosphonium hexafluorophosphate, $CH_2Cl_2$=dichloromethane, $CH_3I$=methyl iodide, $CCl_4$=tetrachloromethane, DIBAH=di-i-butylaluminium hydride, DMA=dimethylacetamide, DMF=dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3N$=triethylamine, eq=equivalents, HOBT=1-hydroxybenzo-triazole, Huenig's base=$iPr_2NEt$=N-ethyl diisopropylamine, LAH=lithium aluminum hydride, MeOH=methanol, NaH=sodium hydride, $NaBH_4$=sodium borohydride, NMM=N-methylmorpholine, NaI=sodium iodide, NaCl=sodium chloride, $PtO_2$=platinum dioxide, RT=room temperature, TBME=t-butyl methyl ether, THF=tetrahydrofuran. All reactions were performed under argon.

Example 1

1.1

To a suspension of 50 g (0.33 mol) of trans-4-aminocyclohexanol-hydrochloride and 77 g (0.726 mol, 2.2 eq) of $Na_2CO_3$ in 650 mL of THF and 150 mL of water, 51.2 mL (0.363 mol, 1.1 eq) of benzyl chloroformate were added at 5° C. over a period of 20 min. The reaction mixture was stirred at RT for 2 h, diluted with EtOAc and the phases were separated. The organic layer was washed with brine, dried over $Na_2SO_4$, filtered and evaporated. Trituration from n-hexane yielded 162.4 g (98%) of trans-4-hydroxy-cyclohexylcarbamic acid benzyl ester as white crystals, MS: 249 (M) [in analogy to Venuti et al., J.Med.Chem. 30:303–318 (1987)].

1.2

To a suspension of 37.9 g (0.94 mol, 2.0 eq) of LAH in 1.3 L of THF was added a suspension of 117 g (0.47 mol) of trans-4-hydroxy-cyclohexylcarbamic acid benzyl ester in 1 L of THF over a period of 6 h via a cannula keeping the temperature between 5–10° C. The reaction mixture was refluxed over night, and a mixture of $Na_2SO_4$, silica gel and water (160 g, 50 g, 80 mL) was added. The suspension was stirred for additional 30 min, filtered and concentrated. The crude material was titurated with n-hexane to yield 27.9 g (46%) of trans-4-methylamino-cyclohexanol. Column chromatography of the mother liquor on silica gel yielded additional 17.1 g (28%) of trans-4-methylamino-cyclohexanol as white solid, MS: 129 (MH$^+$) [in analogy to Venuti et al., J.Med.Chem. 30:303–318 (1987)].

1.3

To 3 g (23.2 mmol) of trans-4-methylamino-cyclohexanol in 120 mL of $CH_2Cl_2$ were added 4.2 mL (24.4 mmol, 1.05 eq) of N,N-diisopropylethylamine followed by 5.96 g (24.4 mmol, 1.05 eq) of 4-(trifluoromethyl)-benzenesulfonyl chloride in 50 mL of $CH_2Cl_2$. The mixture was stirred at RT over night and the organic phase was extracted with 1M $KHSO_4$, followed by 5% $NaHCO_3$. The combined organic phases were washed with brine, dried over $Na_2SO_4$ and evaporated. Column chromatography on silica gel with n-hexane:EtOAc 1:1 as eluent yielded 6.0 g (77%) of trans-N-(4-hydroxy-cyclohexyl)-N-methyl-4-trifluoromethyl-benzenesulfonamide as off-white solid, MS: 338 (MH$^+$).

1.4

At 0° C. to a solution of 0.62 g (5.9 mmol) of methyl beta-hydroxypropionate in 4.5 mL of $CH_2Cl_2$ was added 1.4 mL (6.4 mmol, 2.4 eq) of 2,6-di-tert-butylpyridine, followed by 1.03 mL (6.2 mmol, 2.4 eq) of trifluoromethane sulfonic acid anhydride. The solution was stirred at that temperature for 2.5 h, was concentrated, and the residue was dissolved in 5 mL of nitromethane. To this solution 1 g (2.96 mmol) of trans-N-(4-hydroxy-cyclohexyl)-N-methyl-4-trifluoromethyl-benzenesulfonamide and 1.3 mL (5.9 mmol, 2.0 eq) of 2,6-di-tert-butylpyridine in 10 mL of nitromethane were added. The solution was stirred at 60° C. for 3 h, diluted with EtOAc and 1M $KHSO_4$. The inorganic phase was extracted with EtOAc, the combined organic phases were washed with a saturated aqueous solution of $NaHCO_3$, brine and were dried over $Na_2SO_4$ and evaporated. Column chromatography on silica gel with EtOAc/n-hexane 1:3 gave 1.2 g (95%) of trans-3-{4-[methyl-(4-trifluoromethyl-benzenesulfonyl)-amino]-cyclohexyloxy}-propionic acid methyl ester as light yellow oil, MS: 424 (MH$^+$).

1.5

1.14 g (2.7 mmol) of trans-3-{4-[methyl-(4-trifluoromethyl-benzenesulfonyl)-amino]-cyclohexyloxy}-propionic acid methyl ester in 27 mL of THF were treated with 27 mL of 1M LiOH at RT for 1 h. By adding 1M $KHSO_4$ the solution was acidified, and the mixture was extracted with EtOAc. The organic phase was washed with brine, dried over $Na_2SO_4$ and evaporated to give 1.1 g (quantitative) of trans-3-{4-[methyl-(4-trifluoromethyl-benzenesulfonyl)-amino]-cyclohexyloxy}-propionic acid as colorless oil, MS: 408 (M–H)$^-$.

1.6

100 mg (0.24 mmol) of trans-3-{4-[methyl-(4-trifluoromethyl-benzenesulfonyl)-amino]-cyclohexyloxy}-propionic acid in 3 mL of $CH_2Cl_2$ were treated with 21.3 mg (0.36 mmol, 1.5 eq) of 4-hydroxypiperidine and 0.40 mL (0.36 mmol, 1.5 eq) of NMM. The solution was cooled to 0° C. and 60.9 mg (0.31 mmol, 1.3 eq) of EDCI and 7.5 mg (0.05 mmol, 0.2 eq) of HOBT were added. The mixture was stirred at RT over night, and was then partitioned between $CH_2Cl_2$ and a saturated aqueous solution of $Na_2CO_3$. The organic phase was washed with a solution of $KHSO_4$ and brine, dried over $Na_2SO_4$ and evaporated. Column chromatography with $CH_2Cl_2$:MeOH 98:2 gave 97.1 mg (81%) of trans-N-{4-[3-(4-hydroxy-piperidin-1-yl)-3-oxo-propoxy]-cyclohexyl}-N-methyl-4-trifluoromethyl-benzenesulfonamide as white powder, MS: 493 (MH$^+$).

1.7

Analogously to example 1.6, from trans-3-{4-[methyl-(4-trifluoromethyl-benzenesulfonyl)-amino]-cyclohexyloxy}-propionic acid and 4-(hydroxymethyl)-piperidine was prepared trans-N-{4-[3-(4-hydroxymethyl-piperidin-1-yl)-3-oxo-propoxy]-cyclohexyl}-N-methyl-4-trifluoromethyl-benzenesulfonamide as white viscous oil, MS: 507 (MH$^+$).

1.8

Analogously to example 1.6, from trans-3-{4-[methyl-(4-trifluoromethyl-benzenesulfonyl)-amino]-cyclohexyloxy}-propionic acid and trans-4-methylamino-cyclohexanol was prepared trans,-trans-N-(4-hydroxy-cyclohexyl)-N-methyl-3-{4-[methyl-(4-trifluoromethyl-benzenesulfonyl)-amino]-cyclohexyloxy}-propionamide as white powder, MS: 521 (MH$^+$).

1.9

Analogously to example 1.6, from trans-3-{4-[methyl-(4-trifluoromethyl-benzenesulfonyl)-amino]-cyclohexyloxy}-propionic acid and 2-methylaminoethanol was prepared trans-N-(2-hydroxy-ethyl)-N-methyl-3-{4-[methyl-(4-trifluoromethyl-benzenesulfonyl)-amino]-cyclohexyloxy}-propionamide as white oil, MS: 467 (MH$^+$).

1.10

Analogously to example 1.6, from trans-3-{4-[methyl-(4-trifluoromethyl-benzenesulfonyl)-amino]-cyclohexyloxy}-propionic acid and ethanolamine was prepared trans-N-(2-hydroxy-ethyl)-3-{4-[methyl-(4-trifluoromethyl-benzenesulfonyl)-amino]-cyclohexyloxy}-propionamide as off-white oil, MS: 453 (MH$^+$).

1.11

Analogously to example 1.6, from trans-3-{4-[methyl-(4-trifluoromethyl-benzenesulfonyl)-amino]-cyclohexyloxy}-propionic acid and 2-(ethylamino)-ethanol was prepared trans-N-ethyl-N-(2-hydroxy-ethyl)-3-{4-[methyl-(4-trifluoromethyl-benzenesulfonyl)-amino]-cyclohexyloxy}-propionamide as white oil, MS: 481 (MH$^+$).

1.12

Analogously to example 1.6, from trans-3-{4-[methyl-(4-trifluoromethyl-benzenesulfonyl)-amino]-cyclohexyloxy}-propionic acid and 2-amino-1-propanol was prepared trans-N-(2-hydroxy-1-methyl-ethyl)-3-{4-[methyl-(4-trifluoromethyl-benzenesulfonyl)-amino]-cyclohexyloxy}-propionamide as off-white foam, MS: 467 (MH$^+$).

Example 2

2.1

Analogously to example 1.6, from trans-3-{4-[methyl-(4-trifluoromethyl-benzenesulfonyl)-amino]-cyclohexyloxy}-propionic acid and ethyl 3-(N-methylamino) propionate was prepared trans-3-[methyl-(3-{4-[methyl-(4-trifluoromethyl-benzenesulfonyl)-amino]-cyclohexyloxy}-propionyl)-amino]-propionic acid ethyl ester as green yellow oil, MS: 523 (MH$^+$).

2.2

181 mg (4.78 mmol, 10 eq) of NaBH$_4$ were added portionwise to a solution of 250 mg (0.48 mmol) of trans-3-[methyl-(3-{4-[methyl-(4-trifluoromethyl-benzenesulfonyl)-amino]-cyclohexyloxy}-propionyl)-amino]-propionic acid ethyl ester in 6 mL of a mixture of THF:MeOH (1:1) at 0° C. The reaction mixture was stirred at RT for 4 h. Water was added and the reaction was extracted with CH$_2$Cl$_2$. The combined organic phases were dried over Na$_2$SO$_4$, filtered and evaporated. The crude product was purified by flash chromatography with a gradient of CH$_2$Cl$_2$:MeOH 98:2 to 95:5 to yield 55 mg (24%) of trans-N-(3-hydroxy-propyl)-N-methyl-3-{4-[methyl-(4-trifluoromethyl-benzenesulfonyl)-amino]-cyclohexyloxy}-propionamide as colorless oil, MS: 481(MH$^+$).

2.3

Analogously to examples 2.1 and 2.2, from trans-3-{4-[methyl-(4-trifluoromethyl-benzenesulfonyl)-amino]-cyclohexyloxy}-propionic acid and β-alanine methylester-hydrochloride was prepared trans-N-(3-hydroxy-propyl)-3-{4-[methyl-(4-trifluoromethyl-benzenesulfonyl)-amino]-cyclohexyloxy}-propionamide as colorless oil, MS: 467 (MH$^+$).

Example 3

3.1

13.32 g (103 mmol) of trans-4-methylamino-cyclohexanol were dissolved in isopropanol and treated with 24.75 g (113.4 mmol) of di-tert-butyl-dicarbonate in CH$_2$Cl$_2$. The reaction mixture was stirred at RT over night, concentrated to yield 23.3 g (98%) of trans-(4-hydroxy-cyclohexyl)-methyl-carbamic acid tert-butyl ester as white solid, MS: 229 (M$^+$).

3.2

27 g (117.7 mmol) of trans-(4-hydroxy-cyclohexyl)-methyl-carbamic acid tert-butyl ester were dissolved in 500 mL of THF and were treated with 6.8 mL of tri-n-butylphosphine and 10.5 mL (117.7 mmol) of methyl propiolate at 0° C. for 2d. Additional 2.1 mL (23 mmol, 0.2 eq) of methyl propiolate and 3.4 mL (11.8 mmol, 0.1 eq) of tri-n-butylphosphine were added. After stirring for 1 h at RT, the solution was evaporated and the crude product was purified by flash chromatography with n-heptane:EtOAc 3:1. Trituration with n-heptane yielded 26.7 g (73%) of trans-3-[4-(tert-butoxycarbonyl-methyl-amino)-cyclohexyloxy]-acrylic acid methyl ester as white solid, MS: 314 (MH$^+$).

3.3

15.0 g (47.8 mmol) of trans-3-[4-(tert-butoxycarbonyl-methyl-amino)-cyclohexyloxy]-acrylic acid methyl ester in 400 mL of EtOAc were hydrogenated in the presence of 2.0 g of 10% Pd/C for 3 h. After removal of the catalyst and evaporation of the solvent 15.3 g (quantitative) of trans-3-[4-(tert-butoxycarbonyl-methyl-amino)-cyclohexyloxy]-propionic acid methyl ester were isolated as colorless liquid, MS: 316 (MH$^+$).

3.4

15.3 g (48.5 mmol) of trans-3-[4-(tert-butoxycarbonyl-methyl-amino)-cyclohexyloxy]-propionic acid methyl ester in 485 mL of THF were treated with 485 mL of 1M LiOH at RT for 1 h. The solution was acidified by adding 1M KHSO$_4$, and the mixture was extracted with EtOAc. The organic phase was washed with brine, dried over Na$_2$SO$_4$ and evaporated. The crude product was triturated with n-heptane to give trans-3-[4-(tert-butoxycarbonyl-methyl-amino)-cyclohexyloxy]-propionic acid as white solid, MS: 300 (M–H)$^-$.

3.5

Analogously to example 1.6, from trans-3-[4-(tert-butoxycarbonyl-methyl-amino)-cyclohexyloxy]-propionic acid and ethyl 3-(N-methylamino) propionate was prepared trans-3-({3-[4-(tert-butoxycarbonyl-methyl-amino)-cyclohexyloxy]-propionyl}-methyl-amino)-propionic acid ethyl ester as colorless liquid, MS: 415 (MH$^+$).

3.6

Analogously to example 2.2, from trans-3-({3-[4-(tert-butoxycarbonyl-methyl-amino)-cyclohexyloxy]-propionyl}-methyl-amino)-propionic acid ethyl ester was prepared trans-(4-{2-[(3-hydroxy-propyl)-methyl-carbamoyl]-ethoxy}-cyclohexyl)-methyl-carbamic acid tert-butyl ester as colorless liquid, MS: 373 (MH$^+$).

3.7

1 g (2.71 mmol) of trans-(4-{2-[(3-hydroxy-propyl)-methyl-carbamoyl]-ethoxy}-cyclohexyl)-methyl-carbamic acid tert-butyl ester was dissolved in 5 mL of TBME and 5.4 mL of 5M HCl in TBME were added at 0° C. The solution was stirred at RT, additional 1.5 mL of 5M HCl in TBME were added and stirring was continued. Evaporation of the solvent yielded the crude trans-N-(3-hydroxy-propyl)-N-methyl-3-(4-methylamino-cyclohexyloxy)-propionamide-hydrochloride, MS: 273 (MH$^+$).

3.8

To 158 mg (0.5 mmol) of trans-N-(3-hydroxy-propyl)-N-methyl-3-(4-methylamino-cyclohexyloxy)-propionamide-hydrochloride in 3 mL of CH$_2$Cl$_2$ were added 0.44 mL (2.6 mmol, 5 eq) of N,N-diisopropylethylamine followed by 0.14 mg (0.56 mmol, 1.1 eq) of 4-bromo-benzenesulfonyl chloride. The mixture was stirred at RT for 1 h and the organic phase was extracted with 1M KHSO$_4$. The combined organic phases were washed with brine, dried over Na$_2$SO$_4$ and evaporated. Column chromatography on silica gel with a gradient of CH$_2$Cl$_2$:MeOH 98:2 to 95:5 yielded 101 mg (40%) of trans-3-{4-[(4-bromo-benzenesulfonyl)-methyl-amino]-cyclohexyloxy}-N-(3-hydroxy-propyl)-N-methyl-propionamide as colorless oil, MS: 491 (MH$^+$,1Br).

3.9

Analogously to example 3.8, from trans-N-(3-hydroxy-propyl)-N-methyl-3-(4-methylamino-cyclohexyloxy)-propionamide-hydrochloride and 4-chlorobenzenesulfonyl chloride was prepared trans-3-{4-[(4-chloro-benzenesulfonyl)-methyl-amino]-cyclohexyloxy}-N-(3-hydroxy-propyl)-N-methyl-propionamide as colorless oil, MS: 447 (MH$^+$,1Cl).

3.10

To 158 mg (0.5 mmol) of trans-N-(3-hydroxy-propyl)-N-methyl-3-(4-methylamino-cyclohexyloxy)-propionamide-hydrochloride in 3 mL of CH$_2$Cl$_2$ were added 0.43 mL (2.6 mmol, 5 eq) of N,N-diisopropylethylamine followed by 0.08 mL (0.56 mmol, 1.1 eq) of 4-chlorophenyl chloroformate. The mixture was stirred at RT for 1 h, and the solution was added to a mixture of NaHCO$_3$ solution and CH$_2$Cl$_2$. The phases were separated and the inorganic phase was extracted with CH$_2$Cl$_2$. The organic phase was washed with 1M KHSO$_4$. The combined organic phases were washed with brine, dried over Na$_2$SO$_4$ and evaporated. Column chromatography on silica gel with a gradient of CH$_2$Cl$_2$:MeOH 98:2 to 95:5 yielded 105 mg (48%) of trans-(4-{2-[(3-hydroxy-propyl)-methyl-carbamoyl]-ethoxy}-cyclohexyl)-methyl-carbamic acid 4-chloro-phenyl ester as colorless oil, MS: 427 (MH$^+$,1Cl).

3.11

Analogously to example 3.10, from trans-N-(3-hydroxy-propyl)-N-methyl-3-(4-methylamino-cyclohexyloxy)-propionamide-hydrochloride and 4-bromophenyl chloroformate was prepared trans-(4-{2-[(3-hydroxy-propyl)-methyl-carbamoyl]-ethoxy}-cyclohexyl)-methyl-carbamic acid 4-bromo-phenyl ester as colorless oil, MS: 471 (MH$^+$,1Br).

3.12

Analogously to example 3.10, from trans-N-(3-hydroxy-propyl)-N-methyl-3-(4-methylamino-cyclohexyloxy)-propionamide-hydrochloride and 4-trifluoromethylphenyl chloroformate [Papageorgiou et al., Organic Letters 2:1049–1051 (2000)] was prepared trans-(4-{2-[(3-hydroxy-propyl)-methyl-carbamoyl]-ethoxy}-cyclohexyl)-methyl-carbamic acid 4-trifluoromethyl-phenyl ester as colorless oil, MS: 461 (MH$^+$).

Example 4

4.1

Analogously to example 1.6, from trans-3-[4-(tert-butoxycarbonyl-methyl-amino)-cyclohexyloxy]-propionic acid and 2-(methylamino)ethanol was prepared trans-(4-{2-[(2-hydroxy-ethyl)-methyl-carbamoyl]-ethoxy}-cyclohexyl)-methyl-carbamic acid tert-butyl ester as colorless oil, MS: 359 (MH$^+$).

4.2

Analogously to examples 3.7 and 3.10, from trans-(4-{2-[(2-hydroxy-ethyl)-methyl-carbamoyl]-ethoxy}-cyclohexyl)-methyl-carbamic acid tert-butyl ester and 4-bromophenyl chloroformate was prepared trans-(4-{2-[(2-hydroxy-ethyl)-methyl-carbamoyl]-ethoxy}-cyclohexyl)-methyl-carbamic acid 4-bromo-phenyl ester as colorless oil, MS: 457 (MH$^+$, 1Br).

4.3

Analogously to examples 3.7 and 3.10, from trans-(4-{2-[(2-hydroxy-ethyl)-methyl-carbamoyl]-ethoxy}-cyclohexyl)-methyl-carbamic acid tert-butyl ester and 4-fluorophenyl chloroformate was prepared trans-(4-{2-[(2-hydroxy-ethyl)-methyl-carbamoyl]-ethoxy}-cyclohexyl)-methyl-carbamic acid 4-fluoro-phenyl ester as colorless oil, MS: 397 (MH$^+$).

4.4

Analogously to examples 3.7 and 3.10, from trans-(4-{2-[(2-hydroxy-ethyl)-methyl-carbamoyl]-ethoxy}-cyclohexyl)-methyl-carbamic acid tert-butyl ester and 4-chlorophenyl chloroformate was prepared trans-(4-{2-[(2-hydroxy-ethyl)-methyl-carbamoyl]-ethoxy}-cyclohexyl)-methyl-carbamic acid 4-chloro-phenyl ester as colorless oil, MS: 413 (MH$^+$, 1Cl).

4.5

Analogously to examples 3.7 and 3.10, from trans-(4-{2-[(2-hydroxy-ethyl)-methyl-carbamoyl]-ethoxy}-cyclohexyl)-methyl-carbamic acid tert-butyl ester and 4-trifluoromethylphenyl chloroformate [Papageorgiou et al., Organic Letters 2:1049–1051 (2000)] was prepared trans-(4-{2-[(2-hydroxy-ethyl)-methyl-carbamoyl]-ethoxy}-cyclohexyl)-methyl-carbamic acid 4-trifluoromethyl-phenyl ester as colorless oil, MS: 447 (MH$^+$).

4.6

Analogously to examples 3.7 and 3.8, from trans-(4-{2-[(2-hydroxy-ethyl)-methyl-carbamoyl]-ethoxy}-cyclohexyl)-methyl-carbamic acid tert-butyl ester and 4-bromobenzenesulfonyl chloride was prepared trans-3-{4-[(4-bromo-benzenesulfonyl)-methyl-amino]-cyclohexyloxy}-N-(2-hydroxy-ethyl)-N-methyl-propionamide as colorless oil, MS: 477 (MH$^+$, 1Br).

4.7

Analogously to examples 3.7 and 3.8, from trans-(4-{2-[(2-hydroxy-ethyl)-methyl-carbamoyl]-ethoxy}-cyclohexyl)-methyl-carbamic acid tert-butyl ester and 4-chlorobenzenesulfonyl chloride was prepared trans-3-{4-[(4-chloro-benzenesulfonyl)-methyl-amino]-cyclohexyloxy}-N-(2-hydroxy-ethyl)-N-methyl-propionamide as colorless oil, MS: 433 (MH$^+$, 1Cl).

Example 5

5.1

Analogously to example 1.1, from trans-4-methylamino-cyclohexanol and benzyl chloroformate was prepared trans-(4-hydroxy-cyclohexyl)-methyl-carbamic acid benzyl ester as white solid, MS: 263 (M).

5.2

To a suspension of 15.0 g (57 mmol) of trans-(4-hydroxy-cyclohexyl)-methyl-carbamic acid benzyl ester in 230 mL of toluene were added 16.8 mL (114 mmol, 2 eq) of bromo-acetic acid tert-butyl ester and 1.93 g (5.7 mmol, 0.1 eq) of tetra-n-butylammonium hydrogensulfate and 400 mL of 50% aqueous NaOH. The mixture was stirred at RT for 4 h, additional 1.93 g (5.7 mmol, 0.1 eq) of tetra-n-butylammonium hydrogensulfate and 4.2 mL of bromo-acetic acid tert-butyl ester were added and stirring was continued over night. The solution was concentrated and acidified by addition of 400 mL of 37% HCl. The solution was extracted with EtOAc, the organic phase was washed with brine and dried over Na$_2$SO$_4$. The solvent was removed to yield 18.2 g (quantitative) of trans-[4-(benzyloxycarbonyl-methyl-amino)-cyclohexyloxy]-acetic acid as white solid, MS: 320 (M−H)$^-$.

5.3

Analogously to example 1.6, from trans-[4-(benzyloxycarbonyl-methyl-amino)-cyclohexyloxy]-acetic acid and ethyl 3-(N-methylamino) propionate was prepared trans-3-({[4-(benzyloxycarbonyl-methyl-amino)-cyclohexyloxy]-acetyl}-methyl-amino)-propionic acid ethyl ester as white oil, MS: 435 (MH$^+$).

5.4

Analogously to example 2.2, from trans-3-({[4-(benzyloxycarbonyl-methyl-amino)-cyclohexyloxy]-acetyl}-methyl-amino)-propionic acid ethyl ester was prepared trans-(4-{[(3-hydroxy-propyl)-methyl-carbamoyl]-methoxyl}-cyclohexyl)-methyl-carbamic acid benzyl ester as yellow oil, MS: 393 (MH$^+$).

5.5

15.0 g (47.8 mmol) of trans-(4-{[(3-hydroxy-propyl)-methyl-carbamoyl]-methoxy}-cyclohexyl)-methyl-carbamic acid benzyl ester in 400 mL of EtOAc were hydrogenated in the presence of 2.0 g of 10% Pd/C for 3 h. After removal of the catalyst and evaporation of the solvent 15.3 g (quantitative) of trans-N-(3-hydroxy-propyl)-N-methyl-2-(4-methylamino-cyclohexyloxy)-acetamide as white oil, MS: 259 (MH$^+$).

5.6

Analogously to example 3.10, from trans-N-(3-hydroxy-propyl)-N-methyl-2-(4-methylamino-cyclohexyloxy)-acetamide and 4-chlorophenyl chloroformate was prepared trans-(4-{[(3-Hydroxy-propyl)-methyl-carbamoyl]-methoxy}-cyclohexyl)-methyl-carbamic acid 4-chlorophenyl ester as white oil, MS: 413 (MH$^+$, 1Cl).

5.7

Analogously to example 3.10, from trans-N-(3-hydroxy-propyl)-N-methyl-2-(4-methylamino-cyclohexyloxy)-acetamide and 4-trifluoromethyl phenyl chloroformate was prepared trans-(4-{[(3-hydroxy-propyl)-methyl-carbamoyl]-methoxy}-cyclohexyl)-methyl-carbamic acid 4-trifluoromethyl-phenyl ester as colorless oil, MS: 447 (MH$^+$).

5.8

Analogously to example 1.3, from trans-N-(3-hydroxy-propyl)-N-methyl-2-(4-methylamino-cyclohexyloxy)-acetamide and 4-bromobenzenesulfonyl chloride was prepared trans-2-{4-[(4-bromo-benzenesulfonyl)-methyl-amino]-cyclohexyloxy}-N-(3-hydroxy-propyl)-N-methyl-acetamide as white oil, MS: 477 (MH$^+$, 1Br).

5.9

Analogously to example 1.3, from trans-N-(3-hydroxy-propyl)-N-methyl-2-(4-methylamino-cyclohexyloxy)-acetamide and 4-(trifluoromethyl)benzenesulfonyl chloride was prepared trans-N-(3-hydroxy-propyl)-N-methyl-2-{4-[methyl-(4-trifluoromethyl-benzenesulfonyl)-amino]-cyclohexyloxy}-acetamide as white oil, MS: 467 (MH$^+$).

Example 6

6.1

A solution of 20 g (77.7 mmol) of BOC-tranexamic acid in 162 mL of DMA and 320 mL of THF was cooled to 0° C. and treated with 7.46 g (170.99 mmol, 2.2 eq) of NaH (55% in oil) over 30 min. The mixture was warmed to RT, cooled to 0° C. again and treated with 77.42 mL (1243 mmol, 16 eq) of CH$_3$I and warmed to RT overnight. 230 mL (2487.1 mmol, 32 eq) of aqueous 32% NaOH were added at 0° C., the solution was stirred for 1 h at RT and partitioned between Et$_2$O (×3)/H$_2$O. The organic phase was evaporated to remove the DMA. The residue was dissolved in 100 mL of dioxane and treated with 233 mL (233 mmol) of aqueous 1M NaOH at RT, and the solution was stirred overnight. The reaction was partitioned between Et$_2$O (×3)/H$_2$O, the aqueous phase was acidified with aqueous 10% KHSO$_4$ and partitioned between Et$_2$O (×3), washed once with aqueous 10% NaCl, dried over Na$_2$SO$_4$ and evaporated to yield 19.2 g (87%) of trans-4-[(tert-butoxycarbonyl-methyl-amino)-methyl]-cyclohexane-carboxylic acid, MS: 270 (M–H$^-$).

6.2

A solution of 3.86 g (14.23 mmol) of trans-4-[(tert-butoxycarbonyl-methyl-amino)-methyl]-cyclohexanecarboxylic acid was dissolved in 36 mL of dioxane, cooled to 10° C. and treated with 35.5 mL (142.25 mmol, 10 eq) of 4M HCl in dioxane, then warmed to RT. The solution was evaporated after 2 h to ca. 15 mL, cooled to 0° C. and precipitated with ~100 mL of Et$_2$O. The solid precipitate was filtrated, washed with Et$_2$O (×3) and dried under reduced pressure to yield 2.66 g (90%) of trans-4-methylaminomethyl-cyclohexanecarboxylic acid·HCl, MS: 172 (MH$^+$), MP: 261° C.

6.3

0.60 g (2.89 mmol) of trans-4-methylaminomethyl-cyclohexanecarboxylic acid·HCl were mixed with 7.57 mL (36.28 mmol, 12.5 eq) of hexamethyldisilazane and heated under reflux to 140° C. for 2.5 h. The solution was evaporated, dissolved in 6 mL of THF and treated with 0.45 mL (3.18 mmol, 1.1 eq) of 4-chlorophenylchloroformate at 0° C. and stirred at RT overnight. Then 3 mL of water were added at RT followed by 10 mL of 1M NaOH. After stirring for 1 h at RT 15 mL of 1M HCl were added. The solution was then partitioned between EtOAc (×3)/H$_2$O, dried over Na$_2$SO$_4$ and evaporated to yield 0.92 g (98%) of trans-4-{[(4-chloro-phenoxycarbonyl)-methyl-amino]-methyl}-cyclohexane carboxylic acid, MS: 324 (M–H$^-$, 1Cl).

6.4

A solution of 0.09 g (0.276 mmol) of trans-4-{[(4-chloro-phenoxycarbonyl)-methyl-amino]-methyl}-cyclohexanecarboxylic acid in 2.5 mL of CH$_2$Cl$_2$ was treated at RT with 1 drop of DMF. 0.026 mL (0.304 mmol, 1.1 eq) of oxalyl chloride was added within 5 min and stirring was continued for 90 min. The solution was evaporated, redissolved in 2.5 mL of CH$_2$Cl$_2$ and added to a solution of 0.197 mL (2.21 mmol, 7.2 eq) of 3-(methylamino)-1-propanol [Powell et al., Synthesis (1986), (4), 338–40] at 0° C. The reaction was kept over night at RT, then partitioned between Et$_2$O (×3)/aqueous saturated NaHCO$_3$. The organic phases were washed once with aqueous 10% NaCl, dried over Na$_2$SO$_4$ and evaporated. Purification by flash-chromatography on 5 g silica gel (EtOAc:CH$_2$Cl$_2$ 1:9 to 9:1) gave 0.064 g (58%) of pure trans-{4-[(3-hydroxy-propyl)-methyl-carbamoyl]-cyclohexylmethyl}-methyl-carbamic acid 4-chloro-phenyl ester, MS: 397 (MH$^+$, 1Cl).

Example 7

7.1

To a dry-ice cooled solution of 30.0 g (208 mmol) of trans-(4-hydroxymethyl-cyclohexyl)-methanol in 450 mL of tetrahydrofuran was added at –60° C. to –67° C., within 30 min, 130 mL (208 mmol, 1 eq) of 1.6 M n-butyllithium solution (1.6 M in n-hexane). After stirring for 30 min at –78° C., 32.3 g (208 mmol, 1 eq) of tert-butyl-dimethyl-chlorosilane was added within 10 min. After stirring the reaction mixture at –65° C. for 15 min, it was stirred at RT over night and then partitioned between ether, 1M HCl and water. The organic layer was dried over MgSO$_4$, concentrated under reduced pressure and the residue was then chromatographed on silica gel with a 3:1 v/v mixture of n-hexane and EtOAc as the eluent giving 27.7 g (51%) of pure trans-[4-(tert-butyl-dimethyl-silanyloxymethyl)-cyclohexyl]-methanol as colorless viscous oil, MS: 259 (MH$^+$).

7.2

To an ice-cooled solution of 27.6 g (107 mmol) of trans-[4-(tert-butyl-dimethyl-silanyloxymethyl)-cyclohexyl]-methanol and 9.99 mL (128 mmol, 1.2 eq) of methanesulfonyl chloride in 350 mL of CH$_2$Cl$_2$ were added under stirring 29.6 mL (213 mmol, 2 eq) of Et$_3$N within 20 min keeping the temperature at 0–10° C. The reaction mixture was stirred at RT for 1 h. It was then partitioned between CH$_2$Cl$_2$, 1M HCl and water. The CH$_2$Cl$_2$-phase was dried over MgSO$_4$ and concentrated to yield 38.2 g of crude trans-methanesulfonic acid 4-(tert-butyl-dimethyl-silanyloxymethyl)-cyclohexylmethyl ester as colorless viscous oil, MS: 354 (M+NH$_4^+$).

7.3

38.2 g of crude trans-methanesulfonic acid 4-(tert-butyl-dimethyl-silanyloxymethyl)-cyclohexylmethyl ester and 16.7 g (340 mmol, 3.2 eq) of sodium cyanide dissolved in 380 mL of DMF were stirred at 80° C. for 2 h. After cooling the reaction mixture down to RT, it was partitioned between ether and water. The organic layer was dried over MgSO$_4$ and concentrated under reduced pressure and the residue was then purified by chromatography on silica gel with a 9:1 v/v mixture of n-hexane and EtOAc as the eluent giving 24.2 g (80% over two steps) of pure trans-[4-(tert-butyl-dimethyl-silanyloxymethyl)-cyclohexyl]-acetonitrile as colorless viscous oil, MS: 290 (MNa$^+$).

7.4

A solution of 24.2 g (90.5 mmol) of trans-[4-(tert-butyl-dimethyl-silanyloxymethyl)-cyclohexyl]-acetonitrile, 22 mL (270 mmol, 3 eq) of CHCl$_3$ and 2.4 g of PtO$_2$ (Degussa 223) in 250 mL of ethanol was stirred at RT for 20 h under a hydrogen atmosphere. The catalyst was then removed by filtration and the solvent evaporated under reduced pressure to give 17.1 g (97%) of pure trans-[4-(2-amino-ethyl)-cyclohexyl]-methanol·HCl-salt as colorless solid, MS: 158 (MH$^+$).

7.5

At RT to a solution of 17.6 g (90.9 mmol) of trans-[4-(2-amino-ethyl)-cyclohexyl]-methanol·HCl-salt and 13.9 mL (100 mmol, 1.1 eq) of Et$_3$N in 120 mL of CH$_2$Cl$_2$ was added under stirring within 10 min a solution of 21.8 g (100 mmol, 1.1 eq) of di-tert-butyl-dicarbonate in 70 mL of CH$_2$Cl$_2$. After stirring at RT for 3 h, the reaction-mixture was partitioned between CH$_2$Cl$_2$, 1M HCl and water. Then, the CH$_2$Cl$_2$-phase was dried over MgSO$_4$ and concentrated to yield 27.9 g of crude trans-[2-(4-hydroxymethyl-cyclohexyl)-ethyl]-carbamic acid tert-butyl ester as colorless viscous oil, MS: 275 (M+NH$_4^+$).

7.6

A solution of 27.9 g (86.7 mmol) of trans-[2-(4-hydroxymethyl-cyclohexyl)-ethyl]-carbamic acid tert-butyl ester, 41 mL (434 mmol, 5 eq) of acetic anhydride and 35 mL (434 mmol, 5 eq) of pyridine in 140 mL of CH$_2$Cl$_2$ was stirred at RT for 16 h. The reaction mixture was then taken up in ether and washed with 1M HCl, sodium hydrogen carbonate solution and water. Then, the ether-phase was dried over MgSO$_4$ and concentrated to yield 26.0 g of crude trans-acetic acid 4-(2-tert-butoxycarbonylamino-ethyl)-cyclohexylmethyl ester as colorless viscous oil, MS: 200 [(M-(tert-butoxycarbonyl))H$^+$].

7.7

To an ice-cooled and stirred solution of the crude 26.0 g of trans-acetic acid 4-(2-tert-butoxycarbonylamino-ethyl)-cyclohexylmethyl ester and 5.77 mL (92.6 mmol, 1.1 eq) of CH$_3$I in 300 mL of DMF was added within 15 min 4.04 g (92.58 mmol, 1.1 eq) of NaH (55% in oil). After stirring over night at RT, additional 1.65 mL (26.5 mmol, 0.3 eq) of CH$_3$I and 1.16 g (26.5 mmol, 0.3 eq) of NaH were added and the reaction-mixture was then stirred at RT for 1 h. The compound was then partitioned between ether, 1M HCl solution and water. The organic layer was dried over MgSO$_4$ and concentrated under reduced pressure. The residue was then chromatographed on silica gel with a 4:1 v/v mixture of n-hexane and EtOAc as the eluent giving 18.7 g (68% over 3 steps) of pure trans-acetic acid 4-[2-(tert-butoxycarbonyl-methyl-amino)-ethyl]-cyclohexylmethyl ester as colorless viscous oil, MS: 214 [(M-(tert-butoxycarbonyl))H$^+$].

7.8

To a cooled (~15° C.) and stirred solution of 18 g (57.4 mmol) of trans-acetic acid 4-[2-(tert-butoxycarbonyl-methyl-amino)-ethyl]-cyclohexylmethyl ester in 135 mL of dioxane was added within 5 min 63.2 mL (63.2 mmol, 1.1 eq) of aqueous 1M NaOH. The reaction was homogenised with 13 mL of MeOH and 28.7 mL (28.7 mmol, 0.5 eq) of aqueous 1M NaOH after 3 h, then stirred for additional 1.5 h. The reaction was evaporated to remove the dioxane, partitioned between Et$_2$O (×3)/H$_2$O, dried over Na$_2$SO$_4$ and evaporated to yield 17.13 g (quantitative) of trans-[2-(4-hydroxymethyl-cyclohexyl)-ethyl]-methyl-carbamic acid tert-butyl ester, MS: 272 (MH$^+$).

7.9

A solution of 17.1 g (63.1 mmol) of trans-[2-(4-hydroxymethyl-cyclohexyl)-ethyl]-methyl-carbamic acid tert-butyl ester in 60 mL of CCl$_4$, 60 mL of water and 90 mL of acetonitrile were treated with 0.075 g (0.33 mmol, 0.05 eq) of ruthenium (III) chloride-hydrate and 55.4 g (259 mmol, 4.1 eq) of sodium metaperiodate within 30 min. After 6 h the reaction was decanted and washed with CH$_2$Cl$_2$ (×3). The decanted phase was partitioned between CH$_2$Cl$_2$ (×3)/H$_2$O, the organic phase was dried over Na$_2$SO$_4$ and evaporated to yield 17.24 g (96%) of trans-4-[2-(tert-butoxycarbonyl-methyl-amino)-ethyl]-cyclohexanecarboxylic acid, MS: 284 (M–H$^-$).

7.10

A solution of 17.24 g (60.4 mmol) of trans-4-[2-(tert-butoxycarbonyl-methyl-amino)-ethyl]-cyclohexanecarboxylic acid was dissolved in 150 mL of dioxane, cooled to 10° C. and treated with 151 mL (604.1 mmol, 10 eq) of 4M HCl in dioxane, then warmed to RT and stirred for 3 h. The solution was evaporated to ca. 15 mL, precipitated with ~100 mL of Et$_2$O and cooled to 0° C. The solid precipitate was filtrated, washed with Et$_2$O (×3) and dried under reduced pressure to yield 13.55 g (quantitative) of trans-4-(2-methylamino-ethyl)-cyclohexanecarboxylic acid·HCl, MS: 186 (MH$^+$), MP: 212–214° C.

7.11

1.55 g (7.00 mmol) of trans-4-(2-methylamino-ethyl)-cyclohexanecarboxylic acid·HCl were mixed with 18.4 mL (12.56 mmol, 1.8 eq) of hexamethyldisilazane and heated under reflux to 145° C. for 2.5 h. The solution was evaporated, the residue was suspended in THF and treated with 1.07 g (7.70 mmol, 1.1 eq) of 4-chlorophenylchloroformate at 0° C. and the solution was stirred at RT overnight. 10 mL of water was added at RT followed by 10 mL of 1M NaOH. Stirring was continued for 1 h at RT. The organic solvent was evaporated and the residue partitioned between n-hexane (×3)/H$_2$O. The water phase was acidified with 1M HCl and extracted with EtOAc (3×). The organic phase was dried over Na$_2$SO$_4$ and evaporated to yield 1.92 g (81%) of trans-4-{2-[(4-chlorophenoxycarbonyl)-methyl-amino]-ethyl}-cyclohexanecarboxylic acid, MS: 338 (M–H$^-$, 1Cl).

7.12

A solution of 1.02 g (3.00 mmol) of trans-4-{2-[(4-chlorophenoxycarbonyl)-methyl-amino]-ethyl}-cyclohexanecarboxylic acid in 30 mL of CH$_{42}$Cl$_2$ was treated at RT with 2 drops of DMF, followed by 0.28 mL (3.30 mmol, 1.1 eq) of oxalyl chloride within 5 min, and stirring was continued for 90 min. The solution was evaporated, redissolved in 15 mL of CH$_2$Cl$_2$ and added to a solution of 0.80 g (9.00 mmol, 3 eq) of 3-(methylamino)-1-propanol [Powell et al., Synthesis (4) 338–340 (1986)]and 2.09 mL (15.00 mmol, 5 eq) of Et$_3$N in 12 mL of CH$_2$Cl$_2$ at 0° C. The reaction was kept at RT for 1 h then partitioned between Et$_2$O (×3)/ aqueous saturated NaHCO$_3$. The organic phases were washed once with aqueous 10% NaCl, dried over Na$_2$SO$_4$ and evaporated. Purification by flash-chromatography on 90 g silica gel (EtOAc:CH$_2$Cl$_2$ 1:1 to 4:1) gave 0.95 g (77%) of pure trans-(2-{4-[(3-hydroxy-propyl)-methyl-carbamoyl]-cyclohexyl}-ethyl)-methyl-carbamic acid 4-chloro-phenyl ester, MS: 411 (MH$^+$, 1Cl).

7.13

In analogy to example 6.4, trans-4-{2-[(4-chlorophenoxycarbonyl)-methyl-amino]-ethyl}-cyclohexanecarboxylic acid and 2-(methylamino)ethanol were converted to trans-(2-{4-[(2-hydroxy-ethyl)-methyl-carbamoyl]-cyclohexyl}-ethyl)-methyl-carbamic acid 4-chloro-phenyl ester, MS: 397 (MH$^+$, 1Cl).

7.14

In analogy to example 7.12, trans-4-{2-[(4-chlorophenoxycarbonyl)-methyl-amino]-ethyl}-cyclohexanecarboxylic acid and 4-hydroxypiperidine were converted to trans-{2-[4-(4-Hydroxy-piperidine-1-carbonyl)-cyclohexyl]-ethyl}-methyl-carbamic acid 4-chloro-phenyl ester, MS: 423 (MH$^+$, 1Cl).

Example 8

8.1

To an ice-cooled solution of 10 g (36.8 mmol) of trans-[2-(4-hydroxymethyl-cyclohexyl)-ethyl]-methyl-carbamic acid tert-butyl ester in 100 mL of CH$_2$Cl$_2$ were added 3.15 mL (40.5 mmol, 1.3 eq) of methanesulfonyl chloride followed by 6.68 mL (47.9 mmol, 1.3 eq) of triethylamine. Then the reaction mixture was stirred at RT for 1 h. 1M HCl was added, the phases were separated and the inorganic phase was washed with ether. The combined organic phases were washed with water and dried over magnesium sulfate. Concentration of the solution yielded 12.64 g (98%) of trans-methanesulfonic acid 4-[2-(tert-butoxycarbonyl-methyl-amino)-ethyl]-cyclohexylmethyl ester as colorless oil, MS: 367 (M+NH$_4^+$).

8.2

To 12.64 g (36.17 mmol) of trans-methanesulfonic acid 4-[2-(tert-butoxycarbonyl-methyl-amino)-ethyl]-cyclohexylmethyl ester in 100 mL of DMF were added 4.51 g (92 mmol, 2.6 eq) of sodium cyanide, and the solution was stirred at 80° C. for 2 hours. After cooling the reaction mixture to RT, it was partitioned between ether and water. The organic layer was dried over magnesium sulfate and concentrated under reduced pressure to give 10.14 g (quantitative) of crude trans-[2-(4-cyanomethyl-cyclohexyl)-ethyl]-methyl-carbamic acid tert-butyl ester as colorless oil, MS: 298 (M+NH$_4^+$).

8.3

To 10.14 g (36.17 mmol) of trans-[2-(4-cyanomethyl-cyclohexyl)-ethyl]-methyl-carbamic acid tert-butyl ester in 90 mL of CH$_2$Cl$_2$ were added 90 mL (108.5 mmol, 3 eq) of 1.2M DIBAH at –70—-78° C. The solution was stirred at that temperature for 4 h, 40 mL of 4M HCl were added carefully and the solution was slowly warmed to RT. Stirring was continued at RT for 10 min, and the substance was partioned between ether and 1M HCl. The organic phases were washed with water, dried over magnesium sulfate and concentrated under reduced pressure. The crude product was purified by column chromatography with n-hexane: EtOAc 1:3 to yield 7.5 g (73%) of trans-methyl-{2-[4-(2-oxo-ethyl)-cyclohexyl]-ethyl}-carbamic acid tert-butyl ester.

0.66 g (2.3 mmol) of trans-methyl-{2-[4-(2-oxo-ethyl)-cyclohexyl]-ethyl}-carbamic acid tert-butyl ester were dissolved in 2 mL of CCl$_4$, 2 mL of acetonitrile and 3 mL of water. To this mixture were added 2.4 mg (0.012 mmol, 0.01 eq) of anhydrous ruthenium (III) chloride, followed by 2.04 g (9.5 mmol, 4.1 eq) of sodium metaperiodate in small portions. Stirring was continued at RT for 2 h, the mixture was filtered and partitioned between CH$_2$Cl$_2$ and water. The organic phase was washed with water and dried over magnesium sulfate. Column chromatography of the crude product with a gradient of n-heptane: EtOAc 1:4 to 1:1 gave 430 mg (62%) of trans-{4-[2-(tert-butoxycarbonyl-methyl-amino)-ethyl]-cyclohexyl}-acetic acid as colorless oil, MS: 317 (M+NH$_4^+$).

8.4

To a solution of 200 mg (0.67 mmol) of trans-{4-[2-(tert-butoxycarbonyl-methyl-amino)-ethyl]-cyclohexyl}-acetic acid and 0.065 mL (0.8 mmol, 1.2 eq) of 2-(methylamino)-ethanol were added 0.4 mL (3.3 mmol, 5 eq) of 4-ethylmorpholine and 0.31 g (0.7 mmol, 1.05 eq) of BOP at RT. The solution was stirred at RT for 3 h, diluted with ether and 1M HCl was added. The phases were separated and the organic phases were washed with water and brine and dried over magnesium sulfate. Evaporation yielded 234 mg (quantitative) of crude trans [2-(4-{[(2-hydroxy-ethyl)-methyl-carbamoyl]-methyl}-cyclohexyl)-ethyl]-methyl-carbamic acid tert-butyl ester as colorless oil, MS: 357 (MH$^+$).

8.5

220 mg (0.6 mmol) of trans [2-(4-{[(2-hydroxy-ethyl)-methyl-carbamoyl]-methyl}-cyclohexyl)-ethyl]-methyl-carbamic acid tert-butyl ester in 2 mL of CH$_2$Cl$_2$ were treated at RT with 2 mL of 4N HCl in dioxane. After 30 min at this temperature, ether was added to give after filtration 210 mg (quantitative) of trans N-(2-hydroxy-ethyl)-N-methyl-2-[4-(2-methylamino-ethyl)-cyclohexyl]-acetamide as violet gum, MS: 257 (MH$^+$).

8.6

Analogously to example 3.10, from trans N-(2-hydroxy-ethyl)-N-methyl-2-[4-(2-methylamino-ethyl)-cyclohexyl]-acetamide and 4-chlorophenyl chloroformate was prepared trans-[2-(4-{[(2-hydroxy-ethyl)-methyl-carbamoyl]-methyl}-cyclohexyl)-ethyl]-methyl-carbamic acid 4-chloro-phenyl ester as colorless gum, MS: 411 (MH$^+$).

8.7

Analogously to example 8.4, from trans {4-[2-(tert-butoxycarbonyl-methyl-amino)-ethyl]-cyclohexyl}-acetic acid and 3-(methylamino)-1-propanol [Powell et al., Synthesis (4) 338–340 (1986)] was prepared trans [2-(4-{[(3-hydroxy-propyl)-methyl-carbamoyl]-methyl}-cyclohexyl)-ethyl]-methyl-carbamic acid tert-butyl ester as light yellow oil, MS: 371 (MH$^+$).

8.8

Analogously to example 8.5, from trans [2-(4-{[(3-hydroxy-propyl)-methyl-carbamoyl]-methyl}-cyclohexyl)-ethyl]-methyl-carbamic acid tert-butyl ester was prepared trans-N-(3-hydroxy-propyl)-N-methyl-2-[4-(2-methylamino-ethyl)-cyclohexyl]-acetamide as light red oil, MS: 271 (MH$^+$).

8.9

Analogously to example 3.10, from trans-N-(3-hydroxy-propyl)-N-methyl-2-[4-(2-methylamino-ethyl)-cyclohexyl]-acetamide and 4-chlorophenyl chloroformate was prepared trans-[2-(4-{[(3-hydroxy-propyl)-methyl-carbamoyl]-methyl}-cyclohexyl)-ethyl]-methyl-carbamic acid 4-chloro-phenyl ester as colorless gum, MS: 425 (MH$^+$).

Example 9

9.1

A solution of 0.41 g (1.20 mmol) of trans-4-{2-[(4-chloro-phenoxycarbonyl)-methyl-amino]-ethyl}-cyclohexanecarboxylic acid in 12 mL of CH$_2$Cl$_2$ was treated at RT with 1 drop of DMF, followed by 0.11 mL (1.32 mmol, 1.1 eq) of oxalyl chloride within 5 min and stirring was continued for 90 min. The solution was evaporated and the residue was redissolved in 12 mL of CH$_2$Cl$_2$. At 0° C. this solution was added to a solution of 0.20 g (1.56 mmol, 1.3 eq) of 3-methylamino-propionic acid ethyl ester and 0.84 mL (6.00 mmol, 5 eq) of Et$_3$N in 4 mL of CH$_2$Cl$_2$. The reaction mixture was kept at RT for 1.5 h, then the substance was partitioned between Et$_2$O (×3)/aqueous 10% KHSO$_4$. The organic phases were washed once with aqueous 10% NaCl, dried over Na$_2$SO$_4$ and evaporated to give 0.51 g (94%) of trans-3-[(4-{2-[(4-chloro-phenoxycarbonyl)-methyl-amino]-ethyl}-cyclohexanecarbonyl)-methyl-amino]-propionic acid ethyl ester, MS: 453 (MH$^+$, 1Cl).

9.2

To a cooled (0° C.) and stirred solution of 0.39 g (0.87 mmol) of trans-3-[(4-{2-[(4-chloro-phenoxycarbonyl)-methyl-amino]-ethyl}-cyclohexanecarbonyl)-methyl-amino]-propionic acid ethyl ester in 2.6 mL of THF was added within 5 min 2.6 mL (2.6 mmol, 3 eq) of aqueous 1M LiOH and the solution was stirred at RT for 2.5 h. The reaction was partitioned between Et$_2$O (×3)/aqueous 10% KHSO$_4$. The organic phase was washed with 10% NaCl, dried over Na$_2$SO$_4$ and evaporated to yield 0.38 g (quantitative) of trans-3-[(4-{2-[(4-chloro-phenoxycarbonyl)-methyl-amino]-ethyl}-cyclohexanecarbonyl)-methyl-amino]-propionic acid, MS: 425 (MH$^+$, 1Cl).

9.3

A solution of 0.088 g (0.20 mmol) of trans-3-[(4-{2-[(4-chloro-phenoxycarbonyl)-methyl-amino]-ethyl}-cyclohexanecarbonyl)-methyl-amino]-propionic acid in 2 mL of CH$_2$Cl$_2$ was treated at RT with 1 drop of DMF, followed by 0.019 mL (0.22 mmol, 1.1 eq) of oxalyl chloride and stirring was continued for 90 min. The solution was evaporated, the residue was redissolved in 2.5 mL of CH$_2$Cl$_2$ and added to a solution of 0.25 mL (2.00 mmol, 10 eq) of methylamine (33% solution in EtOH) in 2 mL of CH$_2$Cl$_2$ at 0° C. The reaction mixture was stirred at 0° C. for 3/4 h, then partitioned between Et$_2$O (×3)/aqueous 10% KHSO$_4$. The organic phases were washed once with aqueous 10% NaCl, dried over Na$_2$SO$_4$ and evaporated. Purification by flash-chromatography on 20 g silica gel (CH$_2$Cl$_2$:MeOH 98:2 to 95:5) gave 0.042 g (48%) of pure trans-methyl-(2-{4-[methyl-(2-methylcarbamoyl-ethyl)-carbamoyl]-cyclohexyl}-ethyl)-carbamic acid 4-chloro-phenyl ester, MS: 438 (MH$^+$, 1Cl).

9.4

In analogy to example 9.3, trans-3-[(4-{2-[(4-chloro-phenoxycarbonyl)-methyl-amino]-ethyl}-cyclohexanecarbonyl)-methyl-amino]-propionic acid and ammonia (2M in EtOH) gave trans-(2-{4-[(2-carbamoyl-ethyl)-methyl-carbamoyl]-cyclohexyl}-ethyl)-methyl-carbamic acid 4-chloro-phenyl ester, MS: 424 (MH$^+$, 1Cl).

Example 10

10.1

In analogy to example 9.1, trans-4-{2-[(4-chloro-phenoxycarbonyl)-methyl-amino]-ethyl}-cyclohexanecarboxylic acid and 3 eq sarcosinamide-HCl/16 eq Et$_3$N gave trans-{2-[4-(carbamoylmethyl-methyl-carbamoyl)-cyclohexyl]-ethyl}-methyl-carbamic acid 4-chloro-phenyl ester, MS: 409 (MH$^+$, 1Cl).

10.2

In analogy to example 9.1, trans-4-{2-[(4-chloro-phenoxycarbonyl)-methyl-amino]-ethyl}-cyclohexanecarboxylic acid and 3 eq isonipecotamide/5 eq Et$_3$N gave trans-{2-[4-(4-carbamoyl-piperidine-1-carbonyl)-cyclohexyl]-ethyl}-methyl-carbamic acid 4-chloro-phenyl ester, MS: 450 (MH$^+$, 1Cl), MP: 162–165° C., dec.

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
| --- | --- |
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavoring additives and filled into sachets.

What is claimed is:

1. A compound of formula (I)

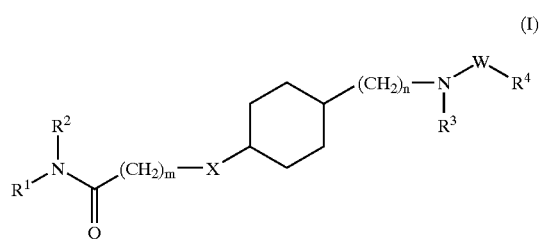

wherein $R^1$ is hydrogen or lower-alkyl;

$R^2$ is selected from hydroxy-lower-alkyl, hydroxy-lower-alkyl substituted with lower-alkyl, hydroxy-cycloalkyl, hydroxy-cycloalkyl substituted with lower-alkyl, carbamoyl-lower-alkyl and carbamoyl-lower alkyl substituted with lower-alkyl; or $R^1$ and $R^2$ are bonded to each other to form a ring together with the nitrogen atom to which they are attached and —$R^1$—$R^2$— is lower-alkylene which is substituted with a group selected from hydroxy, hydroxy-lower-alky and carbamoyl;

$R^3$ is hydrogen or lower-alkyl;

$R^4$ is aryl;

W is selected from CO, COO, CONR$^5$, CSO, CSNR$^5$, SO$_2$, and SO$_2$NR$^5$;

$R^5$ is hydrogen or lower-alkyl;

X is selected from a single bond, O, —CH═CH—, and —C≡C—;

m is 0, 1, 2, 3 or 4, wherein m is not 0 if X is O; and n is 0, 1, 2 or 3, wherein m+n is not more than 5.

2. The compound according to claim 1, wherein X is a single bond or O.

3. The compound according to claim 1, wherein m is 0, 1 or 2.

4. The compound according to claim 3, wherein m is 0 or 2.

5. The compound according to claim 1, wherein n is 0, 1 or 2.

6. The compound according to claim 5, wherein n is 0 or 2.

7. The compound according to claim 1, wherein W is COO or SO$_2$.

8. The compound according to claim 1, wherein $R^1$ is lower-alkyl.

9. The compound according to claim 8, wherein $R^1$ is methyl.

10. The compound according to claim 1, wherein $R^2$ is selected from hydroxy-lower-alkyl, carbamoyl-lower-alkyl, and carbamoyl lower alkyl substituted with lower-alkyl.

11. The compound according to claim 10, wherein $R^2$ is selected from 3-hydroxy-propyl, 2-carbamoyl-ethyl and 2-methylcarbamoyl-ethyl.

12. The compound according to claim 11, wherein $R^2$ is 3-hydroxy-propyl.

13. The compound according to claim 1, wherein $R^1$ and $R^2$ are bonded to each other to form a ring together with the nitrogen atom to which they are attached and $—R^1—R^2—$ is lower-alkylene which is substituted with a group selected from hydroxy, hydroxy-lower-alkyl and carbamoyl.

14. The compound according to claim 13, wherein $—R^1—R^2—$ is $—CH_2—CH_2—CHOH—CH_2—CH_2—$ or $—CH_2—CH_2—CH(CH_2OH)—CH_2—CH_2—$.

15. The compound according to claim 1, wherein $R^3$ is lower-alkyl.

16. The compound according to claim 15, wherein $R^3$ is methyl.

17. The compound according to claim 1, wherein $R^4$ is phenyl substituted with halogen or $CF_3$.

18. The compound according to claim 17, wherein $R^4$ is 4-chloro-phenyl or 4-trifluoromethyl-phenyl.

19. The compound according to any of claim 1, selected from the group consisting of
- trans-N-{4-[3-(4-Hydroxy-piperidin-1-yl)-3-oxo-propoxy]-cyclohexyl}-N-methyl-4-trifluoromethyl-benzenesulfonamide,
- trans-N-{4-[3-(4-Hydroxymethyl-piperidin-1-yl)-3-oxo-propoxy]-cyclohexyl}-N-methyl-4-trifluoromethyl-benzenesulfonamide,
- trans-N-(3-Hydroxy-propyl)-N-methyl-3-{4-[methyl-(4-trifluoromethyl-benzenesulfonyl)-amino]-cyclohexyloxy}-propionamide,
- trans-(2-{4-[(3-Hydroxy-propyl)-methyl-carbamoyl]-cyclohexyl}-ethyl)-methyl-carbamic acid 4-chloro-phenyl ester,
- trans-{2-[4-(4-Hydroxy-piperidine-1-carbonyl)-cyclohexyl]-ethyl}-methyl-carbamic acid 4-chloro-phenyl ester,
- trans-Methyl-(2-{4-[methyl-(2-methylcarbamoyl-ethyl)-carbamoyl]-cyclohexyl}-ethyl)-carbamic acid 4-chloro-phenyl ester, and
- trans-(2-{4-[(2-Carbamoyl-ethyl)-methyl-carbamoyl]-cyclohexyl}-ethyl)-methyl-carbamic acid 4-chloro-phenyl ester.

20. A process for the manufacture of a compound of formula (I)

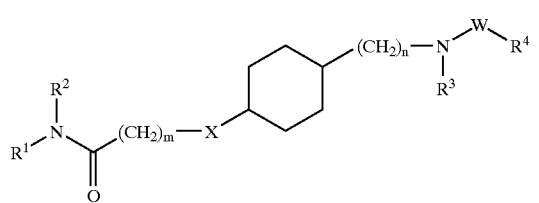

(I)

which process comprises reacting a compound of formula (II)

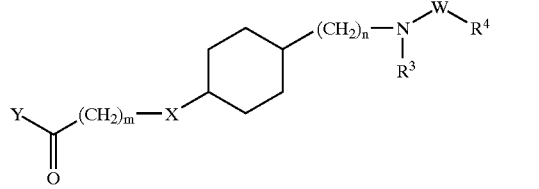

(II)

with a compound $NHR^1R^2$,
wherein,
$R^1$ is hydrogen or lower-alkyl;
$R^2$ is selected from hydroxy-lower-alkyl, hydroxy-lower-alkyl substituted with lower-alkyl, hydroxy-cycloalkyl, hydroxy-cycloalkyl substituted with lower-alkyl, carbamoyl-lower-alkyl and carbamoyl-lower alkyl substituted with lower-alkyl; or $R^1$ and $R^2$ are bonded to each other to form a ring together with the nitrogen atom to which they are attached and $—R^1—R^2—$ is lower-alkylene which is substituted with a group selected from hydroxy, hydroxy-lower-alky and carbamoyl;

$R^3$ is hydrogen or lower-alkyl;

$R^4$ is aryl;

W is selected from CO, COO, $CONR^5$, CSO, $CSNR^5$, $SO_2$, and $SO_2NR^5$;

$R^5$ is hydrogen or lower-alkyl;

X is selected from a single bond, O, $—CH=CH—$, and $—C\equiv C—$;

m is 0, 1, 2, 3 or 4, wherein m is not 0 if X is O;

n is 0, 1, 2 or 3, wherein m+n is not more than 5; and

Y is selected from OH, Cl or Br.

21. A process for the manufacture of a compound process for the manufacture of a compound of formula (I)

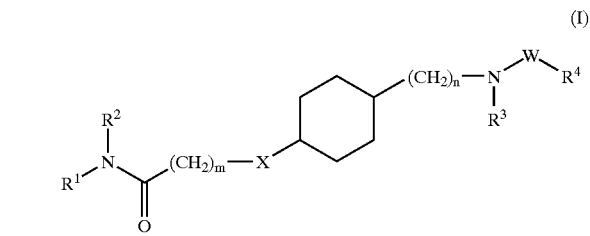

(I)

which process comprises reacting a compound of formula (III)

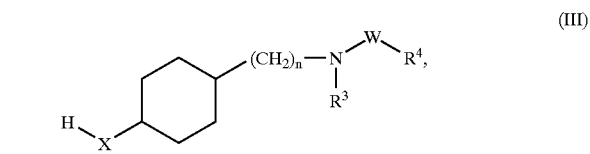

(III)

with a compound $R^1R^2N$ $(C=O)—(CH_2)_m—M$,
wherein,
$R^1$ is hydrogen or lower-alkyl;
$R^2$ is selected from hydroxy-lower-alkyl, hydroxy-lower-alkyl substituted with lower-alkyl, hydroxy-cycloalkyl, hydroxy-cycloalkyl substituted with lower-alkyl, carbamoyl-lower-alkyl and carbamoyl-lower alkyl substituted with lower-alkyl; or $R^1$ and $R^2$ are bonded to each other to form a ring together with the nitrogen atom to which they are attached and $—R^1—R^2—$ is lower-alkylene which is substituted with a group selected from hydroxy, hydroxy-lower-alky and carbamoyl;

$R^3$ is hydrogen or lower-alkyl;

$R^4$ is aryl;

W is selected from CO, COO, $CONR^5$, CSO, $CSNR^5$, $SO_2$, and $SO_2NR^5$;

$R^5$ is hydrogen or lower-alkyl;

X is O;

m is 0, 1, 2, 3 or 4, wherein m is not 0 if X is O;

n is 0, 1, 2 or 3, wherein m+n is not more than 5; and

M is selected from hydroxy, mesylate, tosylate, triflate, Cl, Br and I.

22. A pharmaceutical compositions comprising a compound of formula (I)

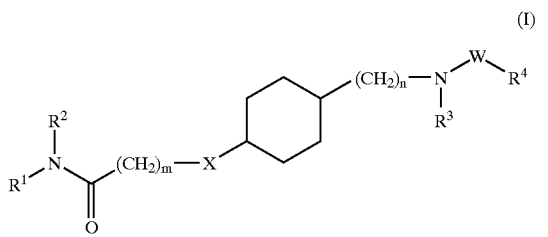

wherein $R^1$ is hydrogen or lower-alkyl;

$R^2$ is selected from hydroxy-lower-alkyl, hydroxy-lower-alkyl substituted with lower-alkyl, hydroxy-cycloalkyl, hydroxy-cycloalkyl substituted with lower-alkyl, carbamoyl-lower-alkyl and carbamoyl-lower alkyl substituted with lower-alkyl; or $R^1$ and $R^2$ are bonded to each other to form a ring together with the nitrogen atom to which they are attached and —$R^1$—$R^2$— is lower-alkylene which is substituted with a group selected from hydroxy, hydroxy-lower-alky and carbamoyl;

$R^3$ is hydrogen or lower-alkyl;

$R^4$ is aryl;

W is selected from CO, COO, CONR$^5$, CSO, CSNR$^5$, SO$_2$, and SO$_2$NR$^5$;

$R^5$ is hydrogen or lower-alkyl;

X is selected from a single bond, O, —CH=CH—, and —C≡C—;

m is 0, 1, 2, 3 or 4, wherein m is not 0 if X is O; and n is 0, 1, 2 or 3, wherein m+n is not more than 5; and a pharmaceutically acceptable carrier.

* * * * *